(12) United States Patent
MacArthur

(10) Patent No.: US 11,857,447 B1
(45) Date of Patent: Jan. 2, 2024

(54) BRACE FOR REDUCING AND STABILIZING FRACTURE IN HUMAN HAND

(71) Applicant: Robert MacArthur, Signal Hill, CA (US)

(72) Inventor: Robert MacArthur, Signal Hill, CA (US)

( * ) Notice: Subject to any disclaimer, the term of this patent is extended or adjusted under 35 U.S.C. 154(b) by 0 days.

(21) Appl. No.: 18/449,655

(22) Filed: Aug. 14, 2023

Related U.S. Application Data

(60) Provisional application No. 63/493,780, filed on Apr. 3, 2023, provisional application No. 63/491,314, filed on Mar. 21, 2023.

(51) Int. Cl.
*A61F 5/01* (2006.01)

(52) U.S. Cl.
CPC .................. *A61F 5/0118* (2013.01)

(58) Field of Classification Search
CPC ........ A61F 5/05875; A61F 5/10; A61F 5/013; A61F 5/0118; A61F 5/05866; A61F 5/05; A61F 2005/0181; A61F 2005/0186; A61F 5/01; A61F 5/0102; A61F 5/0104
USPC .......................................................... 602/22
See application file for complete search history.

(56) References Cited

U.S. PATENT DOCUMENTS

| | | | |
|---|---|---|---|
| 3,170,460 A | 2/1965 | Stilson | |
| 3,794,019 A | 2/1974 | Ritland et al. | |
| 4,243,026 A | 1/1981 | Barber | |
| 4,294,237 A | 10/1981 | Frazier | |
| 4,297,992 A | * | 11/1981 | LaRue .................. A61F 5/0118 602/22 |
| 4,366,812 A | 1/1983 | Nuzzo | |
| 4,441,489 A | 4/1984 | Evans et al. | |
| 4,662,364 A | 5/1987 | Viegas et al. | |
| 4,770,166 A | 9/1988 | Garris | |
| 4,790,301 A | 12/1988 | Silfverskiold | |
| 4,813,406 A | 3/1989 | Ogle | |

(Continued)

FOREIGN PATENT DOCUMENTS

| | | |
|---|---|---|
| DE | 102009034545 B4 | 8/2012 |
| DE | 102013004714 B4 | 3/2016 |
| EP | 3058904 A1 | 8/2016 |

OTHER PUBLICATIONS

MacArthur, Robert, "Brace for Reducing a Metacarpal Fracture", file history of related U.S. Appl. No. 12/245,826, filed Oct. 6, 2008.

*Primary Examiner* — Michelle J Lee
*Assistant Examiner* — Robin Han
(74) *Attorney, Agent, or Firm* — John M. Rogitz; John L. Rogitz

(57) ABSTRACT

A single-splint or two-splint device may be slid onto the finger(s) of a person to help reduce a finger fracture. The device may include a ring coupled to the single or double-splint. The ring may also be coupled to a connector that connects the ring to a wrist band to hold the splinted finger(s) in a desired flexion. Modular pads may also be used across various spaced-apart surfaces of the splint(s) to increase comfort while maintaining stability should swelling increase or decrease. Various combinations of right and left-hand splints of different sizes may even be provided in a kit, with pads of different thicknesses also being provided in the kit. The kit may also include the ring, connector, and wrist band in some examples.

17 Claims, 32 Drawing Sheets

(56) References Cited

U.S. PATENT DOCUMENTS

| | | | |
|---|---|---|---|
| 4,932,396 A * | 6/1990 | Garris | A61F 5/05875 63/15 |
| 4,944,290 A | 7/1990 | Hepburn | |
| 5,183,458 A | 2/1993 | Marx | |
| 5,191,903 A | 3/1993 | Donohue | |
| 5,230,699 A | 7/1993 | Grasinger | |
| 5,346,462 A | 9/1994 | Barber | |
| 5,713,836 A | 2/1998 | O'keefe | |
| 5,947,915 A | 9/1999 | Thibodo | |
| 6,110,136 A | 8/2000 | Belkin | |
| 6,371,932 B1 | 4/2002 | Foote | |
| 6,561,995 B1 | 5/2003 | Thibodo | |
| 6,692,452 B2 | 2/2004 | Chow | |
| 6,808,502 B2 | 10/2004 | Nguyen | |
| 6,932,782 B2 | 8/2005 | Ferraioli | |
| 6,953,441 B2 | 10/2005 | Goumas | |
| 6,988,998 B1 | 1/2006 | Rosa | |
| 7,621,883 B2 | 11/2009 | Duren et al. | |
| 7,758,526 B2 | 7/2010 | DeGould | |
| 7,878,997 B2 | 2/2011 | Bolla | |
| 8,128,586 B2 | 3/2012 | Barnes | |
| 9,301,867 B2 | 4/2016 | Hegland | |
| 9,320,669 B2 | 4/2016 | Bonutti et al. | |
| 10,278,855 B2 | 5/2019 | Salido, III | |
| D930,168 S | 9/2021 | Salinas et al. | |
| 11,576,806 B2 | 2/2023 | Skelton | |
| 2004/0144389 A1 | 7/2004 | Berrehail | |
| 2009/0062708 A1* | 3/2009 | Padova | A61F 5/0118 602/22 |
| 2009/0093744 A1 | 4/2009 | MacArthur | |
| 2009/0204044 A1 | 8/2009 | Benison | |
| 2011/0087145 A1* | 4/2011 | Farrow | A61F 5/0118 602/22 |
| 2012/0289877 A1* | 11/2012 | Hegland | A61F 5/013 602/22 |
| 2017/0128252 A1 | 5/2017 | Dedmond | |
| 2018/0280185 A1* | 10/2018 | Starkey | A61F 5/05875 |
| 2019/0117438 A1 | 4/2019 | Mayer et al. | |
| 2021/0282958 A1 | 9/2021 | Giordana | |

\* cited by examiner

BRACE FOR REDUCING AND STABILIZING FRACTURE IN HUMAN HAND

FIELD

The disclosure below relates to fracture braces for the human hand.

BACKGROUND

As recognized herein, finger and metacarpal fractures are very common. However, as also recognized herein, current methods of treating finger fractures do not allow for optimal healing and/or unduly restrict the use of other parts of the hand. No adequate solutions currently exist for the foregoing problems.

SUMMARY

Accordingly, in one aspect a device includes a splint configured to contact a finger at three spaced-apart locations of the finger to stabilize the finger. The device also includes at least a first foam pad removably insertable between the splint and the finger.

In certain example embodiments, the splint may be a first splint defining a proximal-to-distal dimension and a lateral dimension, the finger may be a first finger, and the device may also include at least a second splint. The second splint may be configured to contact a second finger at three spaced-apart locations of the second finger, and the first and second splints may be connected to each other. The second splint may be lateral to the first splint and the second splint may also be offset from the first splint in the proximal-to-distal dimension, if desired.

Also in certain example embodiments, the device may include at least a second foam pad having a thickness different from a thickness of the first foam pad. Both foam pads may be slit to accept a segment of at least the first splint to removably individually engage the first and second foam pads with the first splint such that a user can select which foam pad to engage with the first splint.

Still further, if desired the device may even include a kit of foam pads of respective different thicknesses. The foam pad(s) may be resilient and deformable if desired.

Additionally, in some examples the locations may be spaced in the proximal-to-distal dimension.

Also in some examples, the first splint may include first, second, and third bands to contact the three locations. The first band may be configured to contact a dorsal location of the finger, and the second and third bands may be configured to contact palmar locations of the finger.

Still further, in certain non-limiting examples the device may also include a hollow ring engageable with a palmar portion of the splint, a wrist band configured to surround a wrist, and a strap to connect the hollow ring and wrist band to hold the finger at a desired flexion.

In another aspect, a device includes a first splint configured to contact a first finger at three spaced-apart locations of the first finger and a second splint configured to contact a second finger at three spaced-apart locations of the second finger. The second splint may be laterally connected to the first splint.

In various example embodiments, the device may also include at least a first foam pad removably insertable between the first splint and the first finger. In specific examples, the device may even include first and second foam pads each removably engageable with a different respective portion of the first splint, where the different respective portions of the first splint may be portions that are spaced from each other in a proximal-to-distal dimension.

Also in various example embodiments, the device may include a first element mechanically engageable with a portion of the first splint, a second element mechanically engageable with a non-finger portion of an arm on which the first and second fingers are located, and a connector to connect the first element and the second element to hold the first finger at a desired flexion. If desired, the portion of the first splint may be a palmar portion of the first splint. Also in certain specific examples, the first element may include a ring, the second element may include a wrist band and/or a hand band, and/or the connector may include a strap. The strap may be adjustable in length to hold the first finger at the desired flexion.

Still further, in certain examples the second splint may be offset from the first splint in a proximal-to-distal dimension. In other examples, the second splint may not be offset from the first splint in the proximal-to-distal dimension.

In still another aspect, a method includes providing a splint configured to contact a finger at three spaced-apart locations of the finger to stabilize the finger. The method also includes providing at least a first foam pad removably insertable between the splint and the finger. The method further includes providing an assembly couplable to the splint to hold the finger at a desired flexion.

The details of the present application, both as to its structure and operation, can best be understood in reference to the accompanying drawings, in which like reference numerals refer to like parts, and in which:

DETAILED DESCRIPTION

Figure 1:
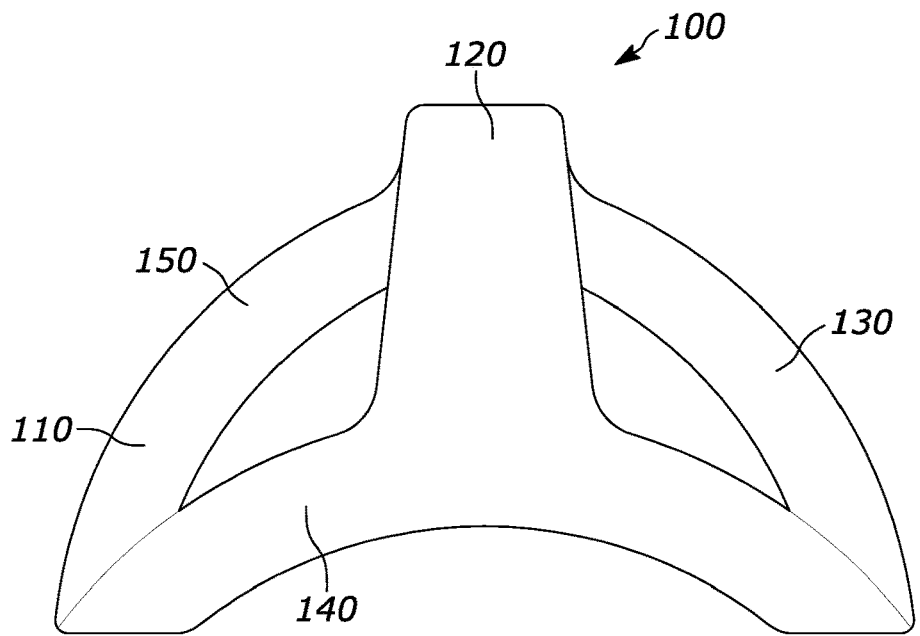
FIG. 1 shows a side perspective view of an example single-splint embodiment consistent with present principles.

Initially in reference to FIG. 1, a side perspective view is shown of a single splint 100 consistent with present principles. The splint 100 may be rigid or semi-rigid. The splint 100 may be made of plastic and/or another polymer such as silicone, hardened rubber, metal such as aluminum, and/or other suitable material. The splint 100 may define a proximal-to-distal dimension and a lateral dimension orthogonal to the proximal-to-distal dimension. The splint 100 may also define a third, dorsal-to-volar dimension. The splint 100 may be integral as formed via injection molding, three-dimensional (3D) printing, and/or other manufacturing methods.

As shown in FIG. 1, the splint 100 may be generally arcuate. The splint 100 may include a first arcuate band 110, a second arcuate band 120, and a third arcuate band 130. When placed on a finger, the second arcuate band 120 is to extend laterally over a dorsal area of a fractured finger joint while the first and third arcuate bands 110, 130 extend laterally under volar areas of the finger that are proximal and distal to the joint.

The bands 110-1130 may be connected to each other via arcuate side members 140, 150 that include center apices pointing up dorsally, with the side members 140, 150 extending between ends of the bands 110-130 in the proximal-to-dorsal dimension. As such, ends of the bands 110, 130 may terminate at integral proximal and distal ends of the respective members 140, 150. Additionally, the center apices of the members 140, 150 may transition to integral ends of the band 120.

As also shown in FIG. 1 and as mentioned above, the bands 110-130 may be spaced apart from each other on the splint 100 in the proximal-to-distal dimension so that the bands 110-130 contact a finger at three spaced-apart locations of the finger, proximal-to-distal, to stabilize the finger for finger fracture recovery. In some specific examples, only three lateral bands may be used (e.g., the bands 110-130) and the bands may contact the finger at only the three spaced-apart locations of the finger and no other locations of the finger. The three spaced-apart locations may therefore be longitudinally spaced from each other along the finger and may not establish other portions of the finger at spaces in between.

As further shown in FIG. 1, the bands 110 and 130 may extend volarly downward to engage volar area/palmar surface locations of the finger, while the band 120 may extend dorsally upward to engage a dorsal area/top surface location of the finger. Thus, in addition to the bands 110-130 being spaced apart from each other in the proximal-to-distal dimension, the bands 110, 1130 may have center apices pointing volarly and the band 120 may have a center apex pointing dorsally.

As for the inner surfaces of the splint 100, they may be smooth and configured to sit flat against the finger itself when engaged therewith. In some examples, proximal-to-distal subsections of the bands 110-130 may be straight in the proximal-to-distal dimension while arcuate in the dorsal/volar-lateral plane. The bands 110-130 may also have a thickness, generally dorsal-volar, that is less than the proximal-to-distal subsections are long.

Figure 2:
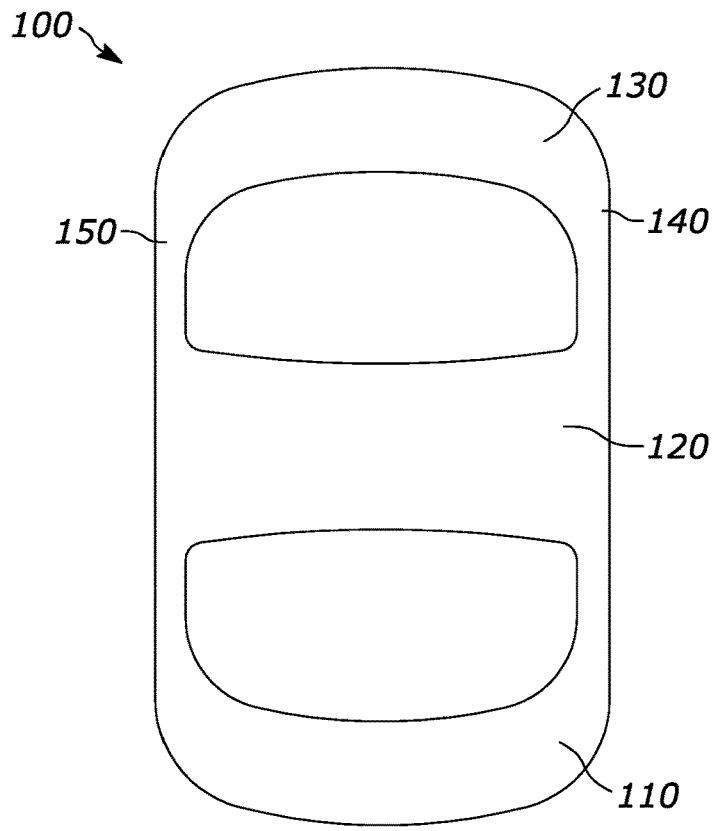
FIG. 2 shows a top perspective view of the single splint consistent with present principles.
Figure 3:
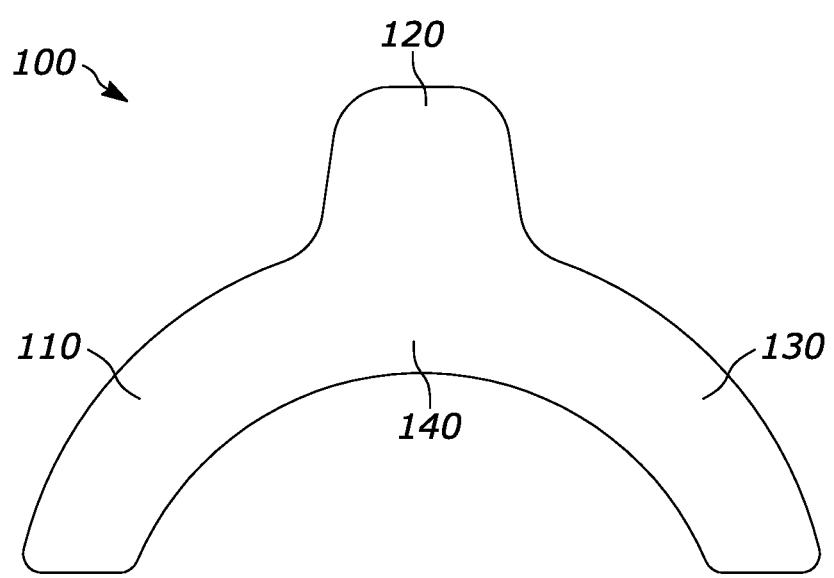
FIG. 3 shows a side elevational view of the single splint consistent with present principles.

FIG. 2 shows the splint 100 again, but from a top perspective view. FIG. 3 shows the splint 100 from a side elevational view.

Figure 4:
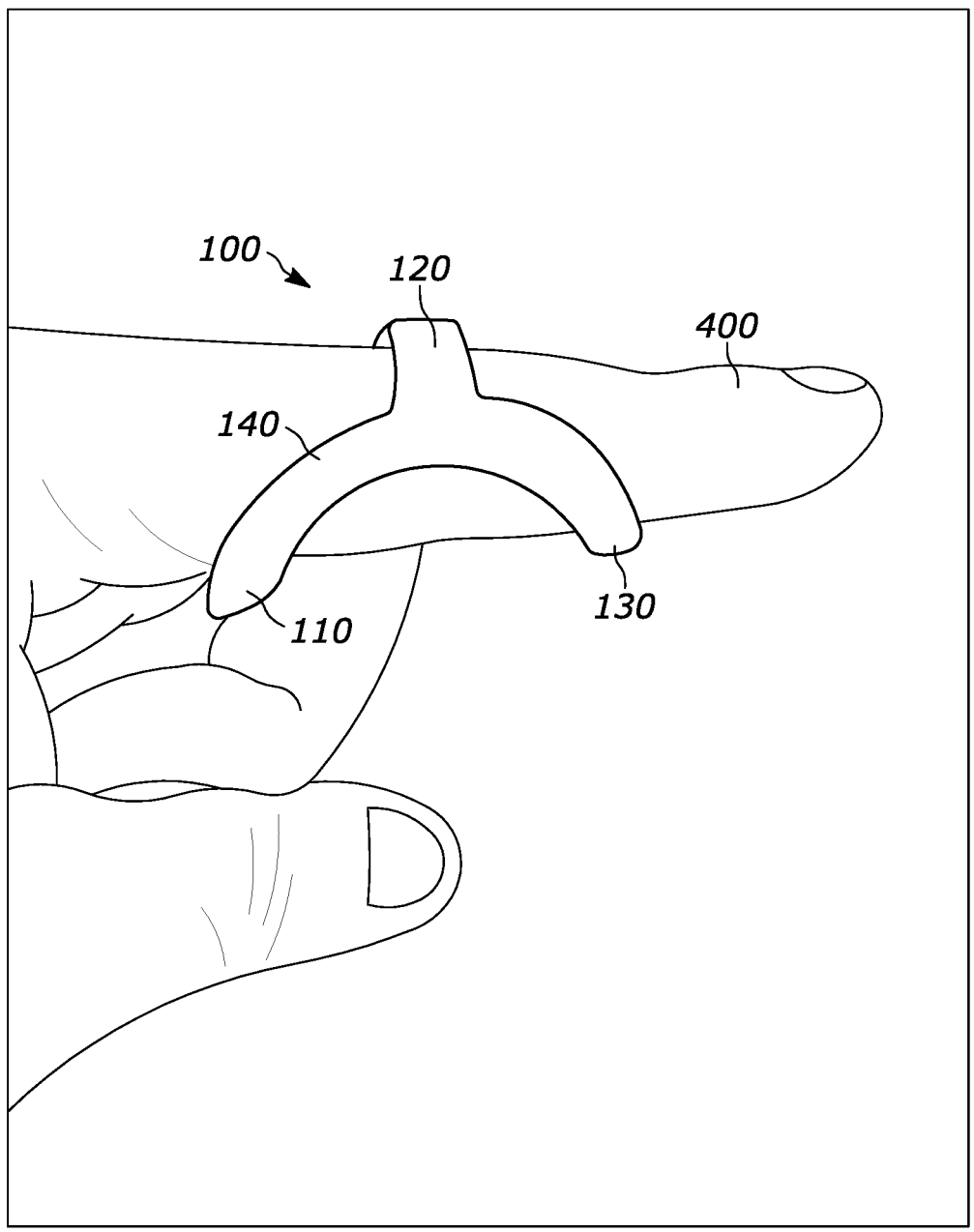
FIGS. 4 and 5 show side views of the single splint as placed on a finger to stabilize a fracture to a proximal phalanx joint consistent with present principles.

FIG. 4 then shows the splint 100 placed on a finger 400 to stabilize a fracture to a proximal phalanx joint of an index finger 400. As may be appreciated from FIG. 4, the band 120 sits flat and smoothly against a dorsal surface of the finger 400 directly above the joint, while bands 110, 130 sit flat and smoothly against spaced-apart volar/palmar surfaces of the finger 400 and the members 140, 150 sit flat and smoothly against side areas of the finger 400.

Figure 5:
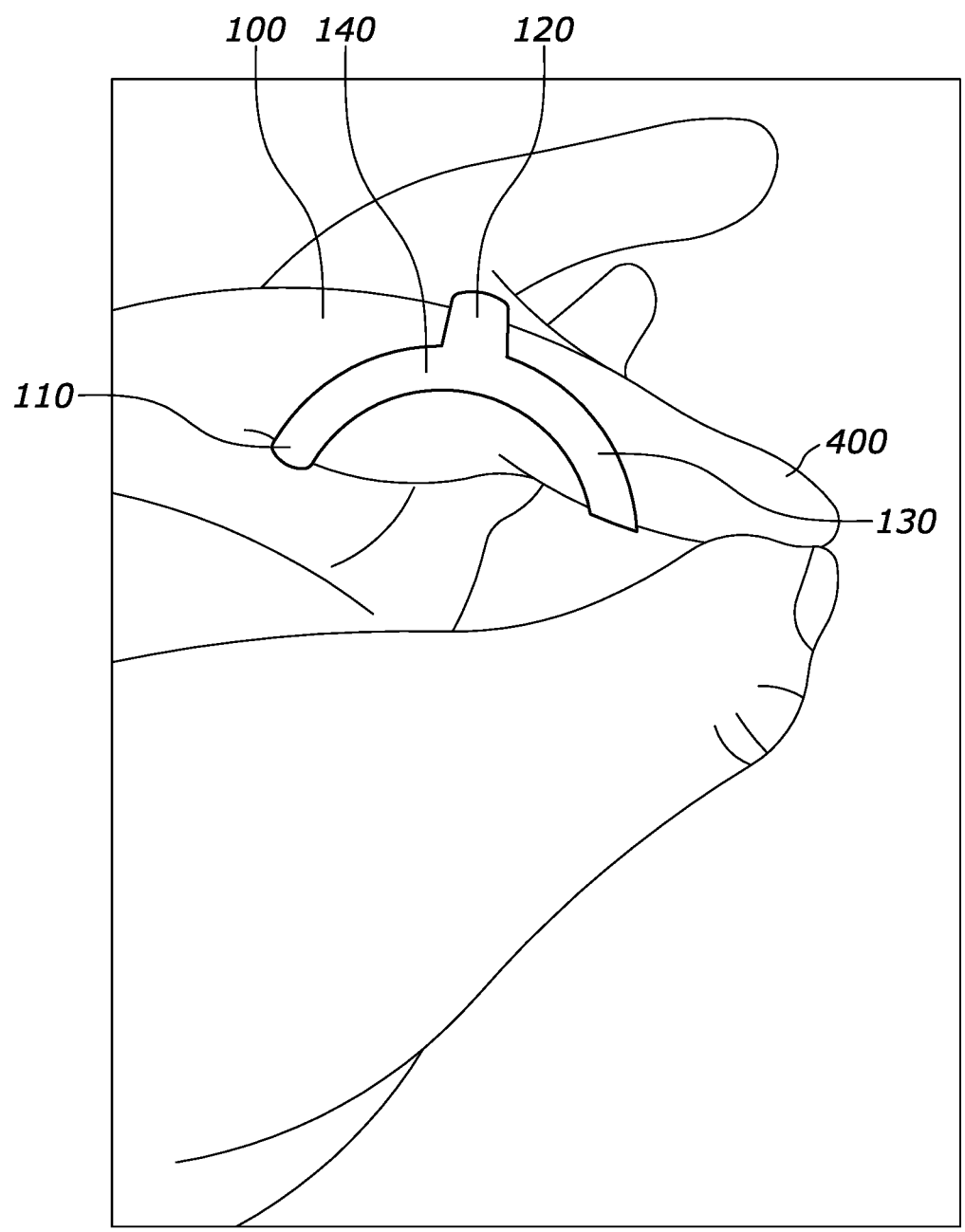

It may be appreciated that the configuration of the splint 100 with the three bands 110-130 may therefore immobilize the joint so that the finger 400 is impeded or prevented from bending at the joint due to the pressure points created by the spaced apart contact of the bands 110-130 with the finger 400. This is further demonstrated in FIG. 5, where the person is attempting to bend his/her finger 400 at the joint.

Figure 6:
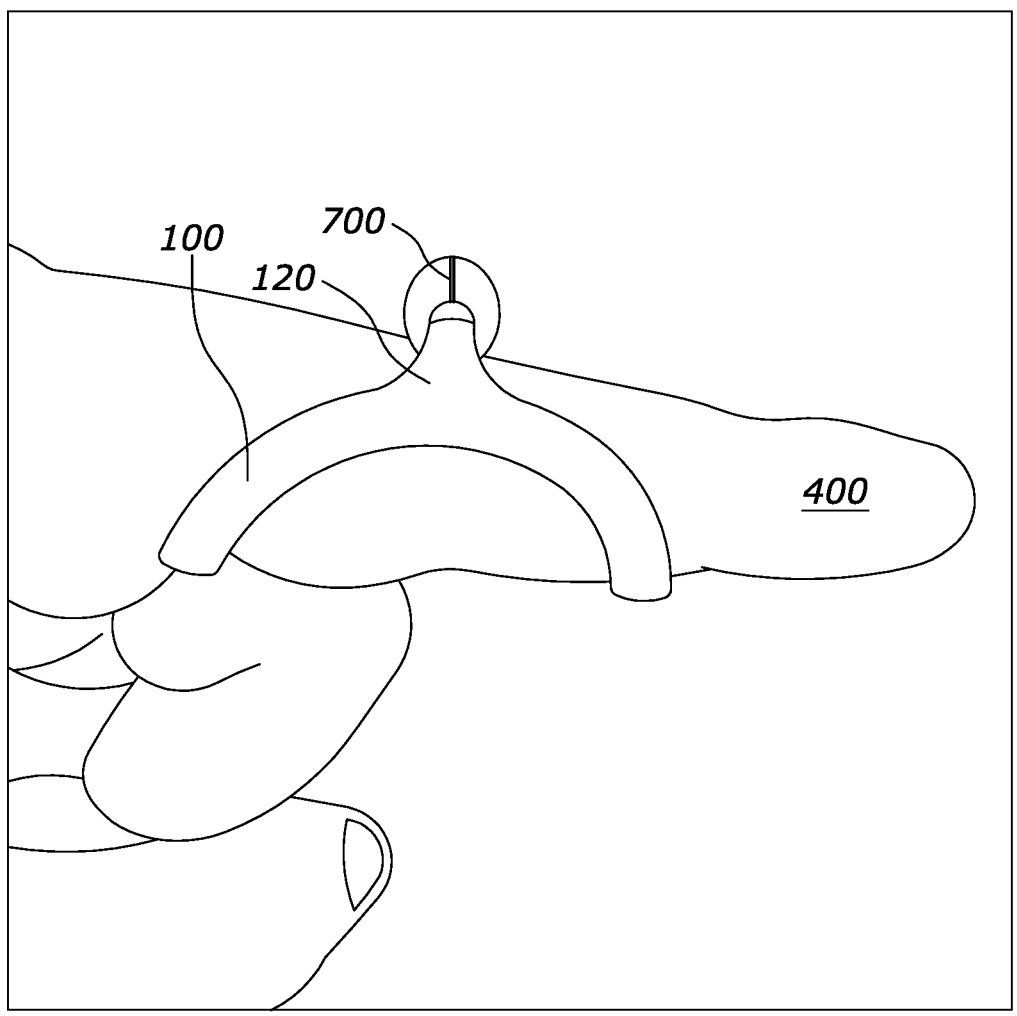
FIGS. 6 and 8 shows side views of the single splint with a foam pad engaged with a dorsal portion of the splint consistent with present principles.
Figure 7:
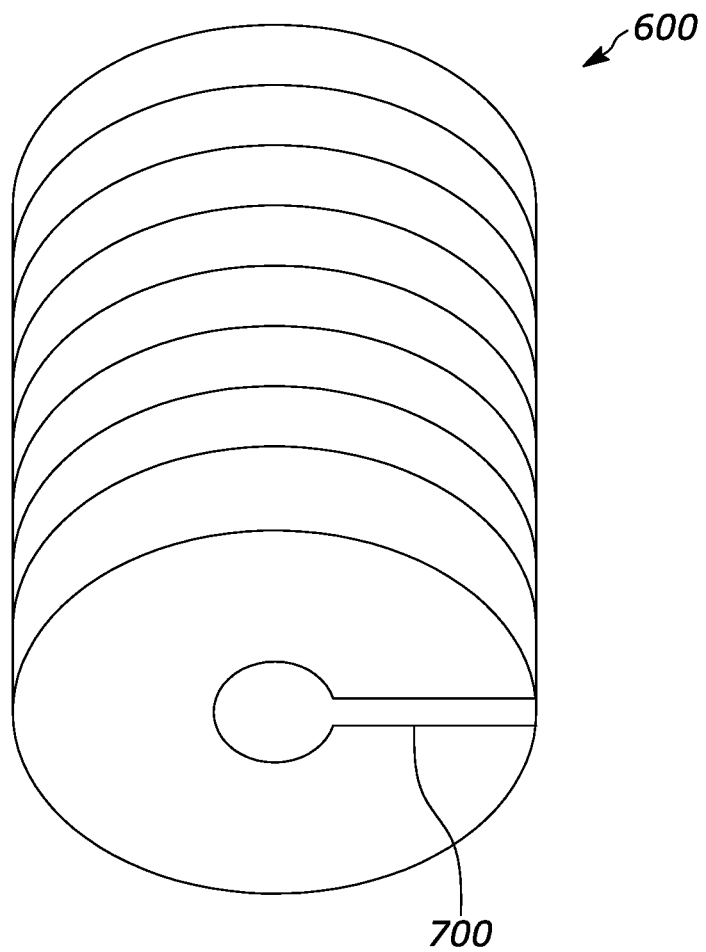
FIG. 7 shows a perspective the foam pad by itself.

FIG. 6 then shows an example embodiment where at least a first foam pad 600 may be configured for removable engagement with the band 120. The pad 600 may be resilient and deformable, and may be configured to circumscribe the band 120 in the dorsal/volar-proximal/distal plane. The pad 600 may also be configured to extend in the lateral dimension along some or all of the band 120 when engaged therewith. The pad 600 may thus be removably insertable between the splint 100 and the finger 400 via a lateral slit 700 or other opening in the pad 600 to accept a segment of the splint 100 (the band 120 or even one of the bands 110, 130). The pad 600 with slit 700 is also shown by itself in the pad perspective view of FIG. 7. And note that while the pad 600 itself may be made of foam as shown, it may additionally or alternatively be made of plastic, fabric, or another suitable material.

Additionally, if desired, external surfaces of the pad 600 may have a smooth exterior finish. The finish may be made of the same material as the insides of the pad 600 (e.g., foam) and/or made of a wrapping such as surgical tape or a mesh. In addition to having a smooth exterior finish, the pad 600 may also be deformable to conform to the exterior contours of the finger 400 to comfortably engage the finger 400 as shown in FIG. 6 when the splint 100 is positioned around a fractured joint. Thus, regardless of what type of material the pad 600 is made of, the pad 600 may be deformable, compressible, and/or spongy to conform to the different contours of the finger 400 around the proximal phalanx joint (or other joint).

Therefore, while different 3D shapes may be used, in many example embodiments the pad 600 may be cylindrical. In other example embodiments it might be arcuate at a same degree or similar degree as the arc of the band 120 itself. But whether cylindrical or arcuate, the respective pad may also, in some but not necessarily all cases, form a hollow inner cylindrical or arcuate area in which a respective band of the splint 100 may reside once the band is slid into the hollow inner area through the aforementioned slit 700. Thus, here the pad 600 may establish a foam tube, cylindrical or arcuate. However, as alluded to above, in other embodiments the pad 600 may be solid on the inside, save for the slit 700.

Either way, the pad 600 might be referred to as a "backer rod" in non-limiting examples. Additionally, example pads 600 of different thicknesses (e.g., for a kit) may be established by respective pads (hollow or not) having a transverse outer diameter of four sixteenths (4/16) of an inch, five sixteenths (5/16) of an inch, and six sixteenths (6/16) of an inch, with a respective slit running longitudinally in a straight line on one side of each pad. The respective slit may extend to a depth of the center point of the respective rod/pad according to the transverse dimension. The slit to the center may therefore result in an effective padding thickness between the finger and respective splint component (e.g., band 120) of two sixteenths (2/16) of an inch, two and half sixteenths (2.5/16) of an inch, and three sixteenths (3/16) of inch, respectively.

Figure 8:
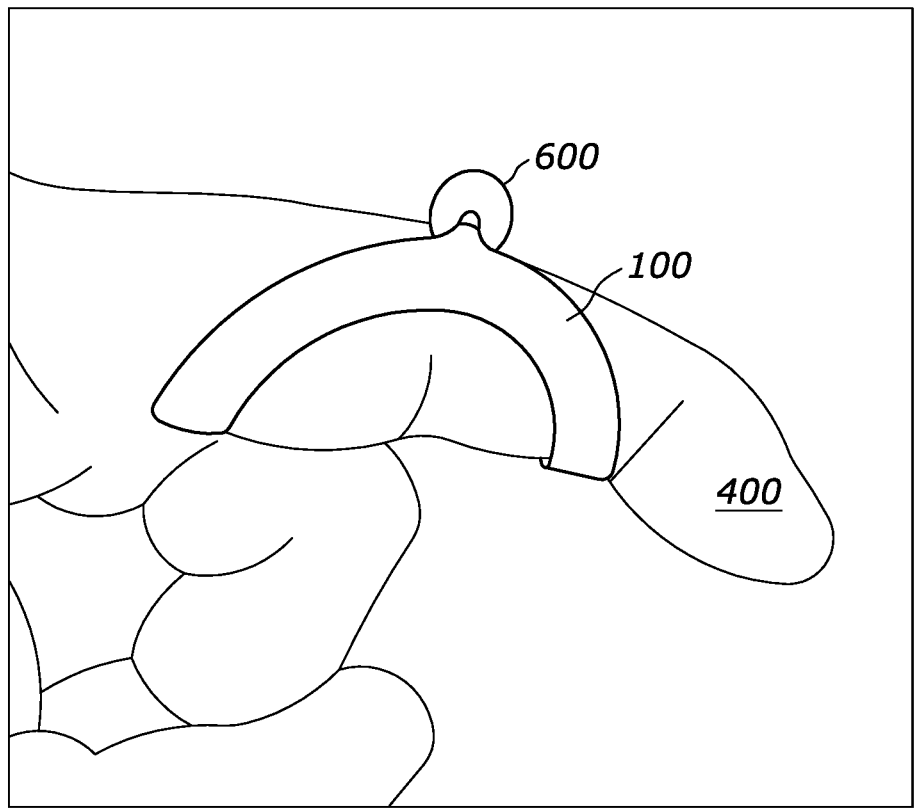

In brief reference to FIG. 8, it may be appreciated that with the pad 600 still engaged with the splint 100, the finger 400 is impeded or prevented from bending at the proximal interphalangeal (PIP) joint despite significant force, in fact enough force to flex through the distal interphalangeal (DIP) joint. In contrast, without the modular pads, a flexion force through the finger may result in flexion motion through the PIP joint. The pads thus demonstrate significant enhancement of the stabilization force on the finger.

In the event of an avulsion of the extensor tendon from the dorsal face of the distal phalanx, without the pads the brace may only immobilize the DIP in neutral position, while applying modular pads with the brace slid distally from the PIP joint to the DIP joint may affect an ideal hyperextension of the DIP joint, the correct position for healing of an extensor tendon avulsion.

Figure 9:
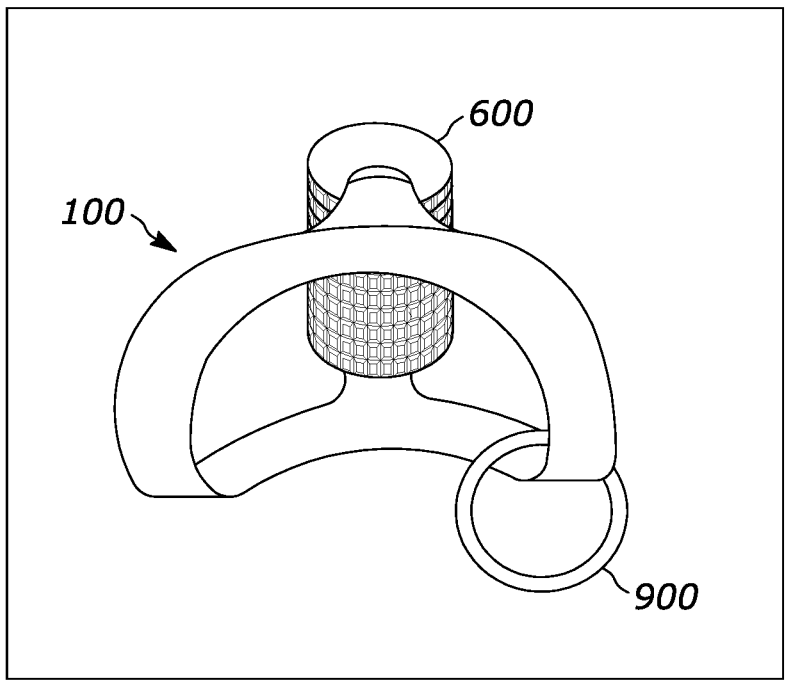
FIG. 9 shows the single splint with both the foam pad and a connector ring consistent with present principles.
Figure 9A:
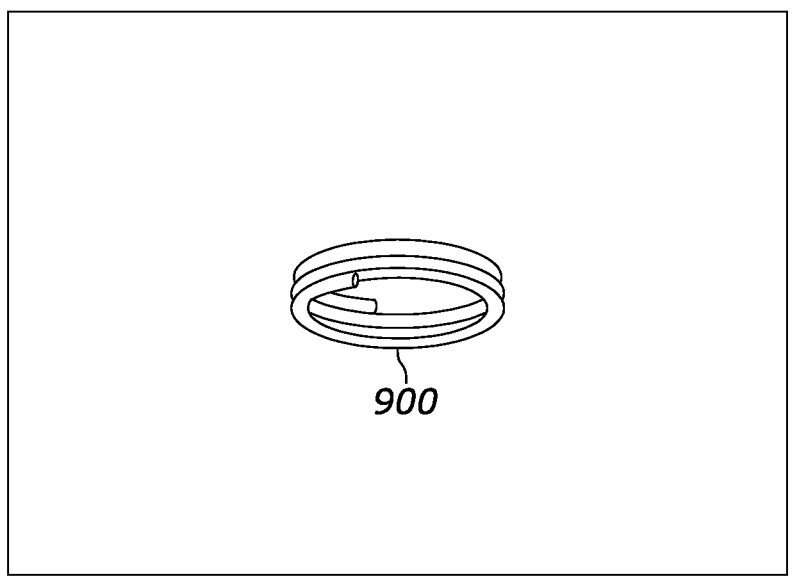
FIG. 9A shows a perspective view of the ring by itself.

Now in reference to FIG. 9, a bottom perspective view is shown of the splint 100 with pad 600. An additional aspect consistent with present principles is also shown in FIG. 9, which is a hollow ring 900 engaged with the splint 100. The hollow ring 900 is also shown by itself in the perspective view of FIG. 9A.

As best shown in FIG. 9, the hollow ring 900 may be removably engaged with a palmar portion of the splint 100. Specifically, the ring 900 may be engaged with the band 110 or band 130. In specific non-limiting examples, a physician or patient may mechanically engage the ring 900 with whichever band 110 or 130 will be used as a distal-most band when the splint 100 is engaged with the finger. As also shown in FIG. 9, the ring 900 may circumscribe the band 110/130 in the dorsal/volar-proximal/distal plane.

Figure 10:
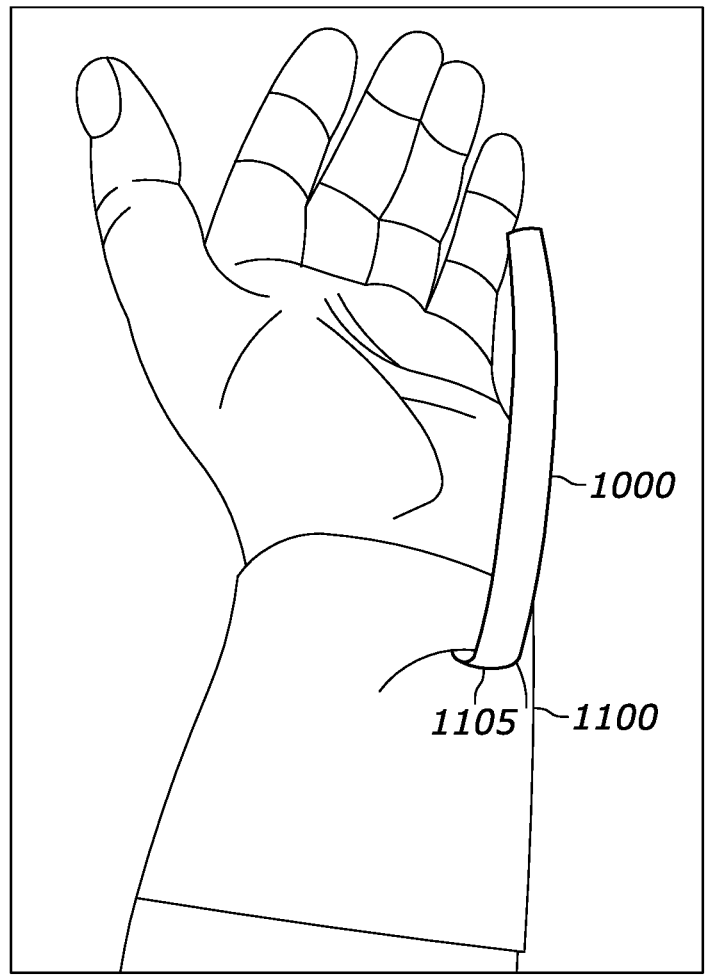
FIG. 10 shows a palmar perspective view of an example connector strap and wrist band for coupling to a finger splint consistent with present principles.

In some examples, the ring 900 may be established by a key ring with a clasp to open and close the ring 900 to engage and disengage the ring 900 with the splint 100. Additionally or alternatively, another type of mechanism may also be used to open and close the ring 900, such as a circle cotter mechanism or kickout ring mechanism. The ring 900 may be opened to both engage the ring 900 with the band 110 or 130, and to also engage the ring 900 with a strap 1000 or other connector as shown in FIG. 10. Additionally, note that the ring 900 itself may be rigid and made of metal, plastic, hardened silicone or another polymer, hardened or even soft rubber, or another suitable material.

Before describing the aforementioned strap 1000 in more detail, also note that another type of element other than a ring 900 may be used instead. For example, the element connecting the splint 100 to the strap 1000 may be established by another strap or other intermediary component between the splint 100 and strap 1000 to mechanically couple the splint 100 to the strap 1000. Or as another example embodiment, the strap 1000 may be coupled directly to the splint 100 without an intermediary component like the ring 900.

In any case, assuming the hollow ring 900 is used and now in reference to FIG. 10, the strap 1000 itself may be adjustable in length and non-rigid (e.g., pliable, flexible, and/or string-like). Once set or locked to a desired length, the strap 1000 may remain at the selected fixed length until further manual adjustment by the physician or patient. The strap 1000 may be made of a flat hard plastic, hard or soft rubber, a string, or other material. In the present example, the strap 1000 is also shaped long and flat as shown.

The length of the strap 1000 itself may be adjusted using a buckle, velcro, buttons, a snapback mechanism, or other mechanism arranged on the strap 1000. For velcro hook-and-loop fasteners, the same or opposing flat surfaces of the strap 1000 may be layered with reciprocal velcro elements, one with hooks and one with loops, to engage each other. Thus, the strap 1000 may be connected to both the ring 900 and to a wrist band 1100, with the opposing ends of the strap 1000 fed through the ring 900 and an opening 1105 in the band 1100 and then extended/folded over each other for the reciprocal velcro components to engage each other (once the strap 1000 has been set at a desired length as looped through both the ring 900 and opening 1105). A similar connection and fixation at desired length may be established using non-velcro elements as well, such as a buckle or buttons as discussed above.

Figure 10A:
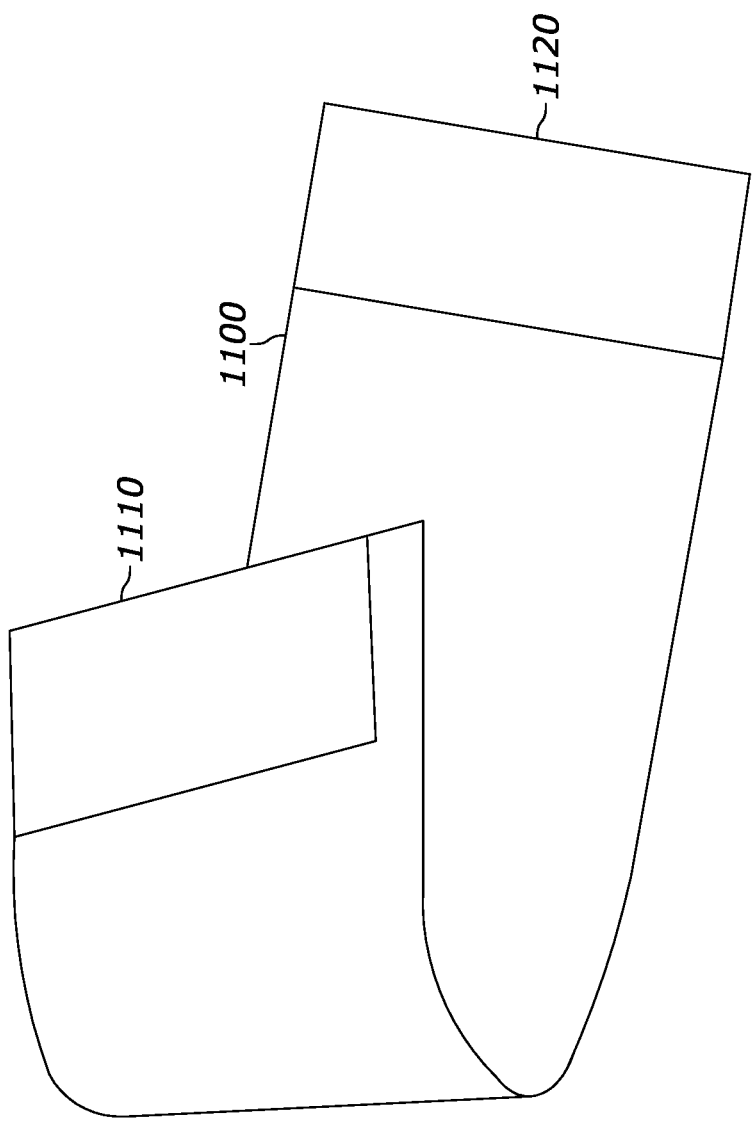
FIG. 10A shows a perspective view of the wrist band by itself and partially folded over on itself consistent with present principles.

Note that FIG. 10A shows the band 1100 by itself for additional illustration. Also note that the opening 1105 may be a slit or even a circular opening. In either case, a grommet made of metal or other material may circumscribe or otherwise surround the inner periphery of the opening 1105 for resilience of the band 1100 when the strap 1000 is engaged therewith.

In cross-reference to FIGS. 10 and 10A, the band 1100 is a wrist band as shown.

However, the band 1100 may also be configured for engagement with other non-finger portions of the arm as well. The band 1100 may be made of a soft, pliable material such as felt and/or other cloth, soft rubber, polyester and/or other polymer, or other suitable material. The band 1100 may be generally rectangular in shape as shown, though other configurations may also be used such as an oval-shaped band. In various examples, the band 1100 may be nine to twelve inches long for an adult-sized band and five and a half to nine inches long for a child-sized band.

The band 1100 may have engagement members 1110, 1120 at opposing end portions according to the band's longitudinal dimension. In some examples, the members 1110, 1120 may be reciprocal hook-and-loop velcro components as shown. In other examples, the members 1110, 1120 might be established by reciprocal button fasteners, a snapback mechanism, or other mechanism.

Describing the hook-and-loop velcro components 1110, 1120 shown in FIG. 10A, a first flat face at a first end portion of the band 1100 may bear a layer of hooks while an opposing, second flat face at a second end portion of the band 1100 may bear a layer of loops. Then as demonstrated by FIG. 10, the ends of the band 1100 may be engaged with each other via the velcro components 1110, 1120 so that the band 1100 circumscribes and surrounds the person's wrist and is fixed thereto until the components 1110, 1120 are manually disengaged from each other. In specific examples, the band 1100 may be engaged with the wrist in a snug fit so that there is little or no slack in the band 1100.

As alluded to above, although a wrist band is shown as the band 1100 according to FIGS. 10 and 10A, the band 1100 may be configured to surround or otherwise mechanically engage with other non-finger portions of the same arm as where the finger fracture is located as well. For example, the band 1100 may be a hand band that laterally circumscribes and surrounds a portion of the person's hand proximal to the metacarpophalangeal joints of the four fingers and distal to the metacarpophalangeal joint of the thumb, with the thumb itself remaining free and not strapped down. Or the band 1100 may be a forearm band that laterally circumscribes and surrounds a portion of the person's forearm proximal to the wrist.

Figure 11:
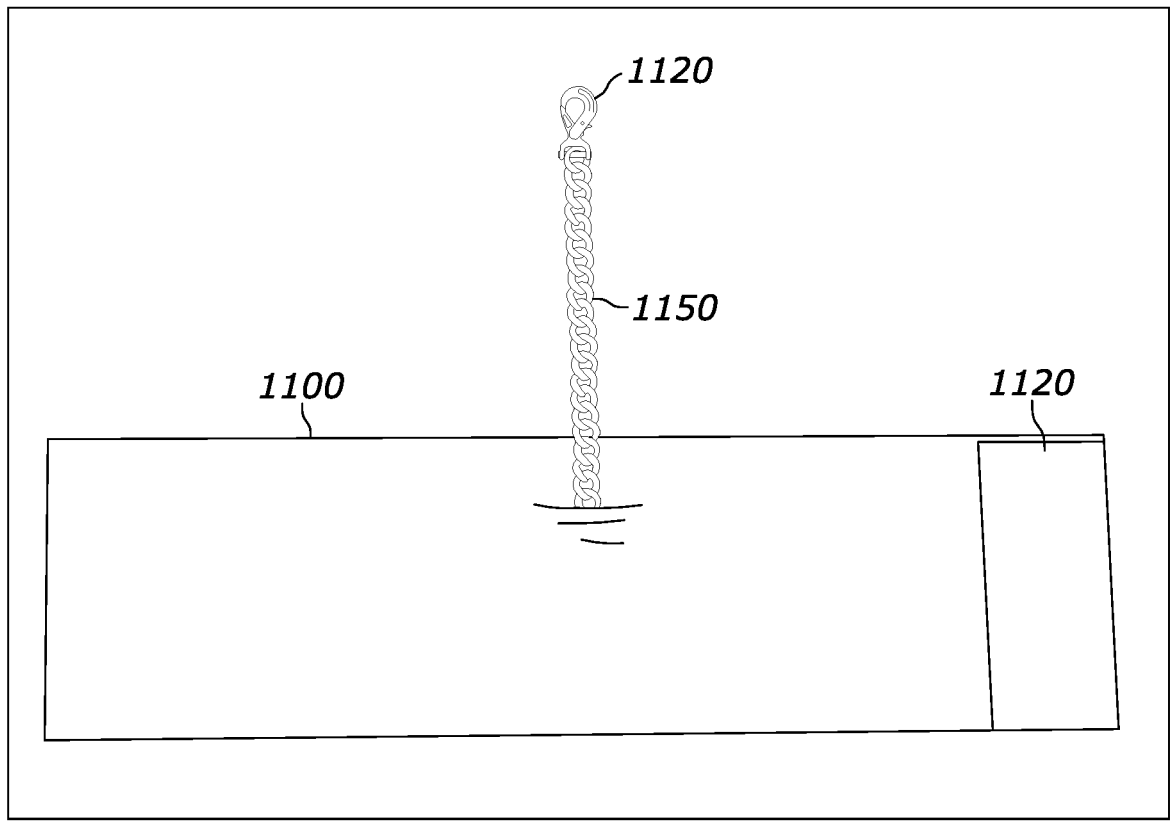
FIG. 11 shows an example where a wrist band is engaged with a connector chain rather than a connector strap consistent with present principles.

Turning to FIG. 11, the band 1100 is again shown, but here the connector used to couple the ring 900 to the band 1100 is a metal chain 1150 rather than a long, flat strap according to FIGS. 10 and 10A. The chain 1150 may be anchored at a first end to a first flat surface of the band 1100 using glue or other fastening mechanism, and/or the chain 1150 may be looped through an opening in the band 1100 like the opening 1105 described above and then anchored or chain-linked to itself.

The chain 1150 may also include a second end terminating in a hook or clasp or other mechanical element 1170 for the chain 1150 to connect to the ring 900 at the second end.

Figure 12:
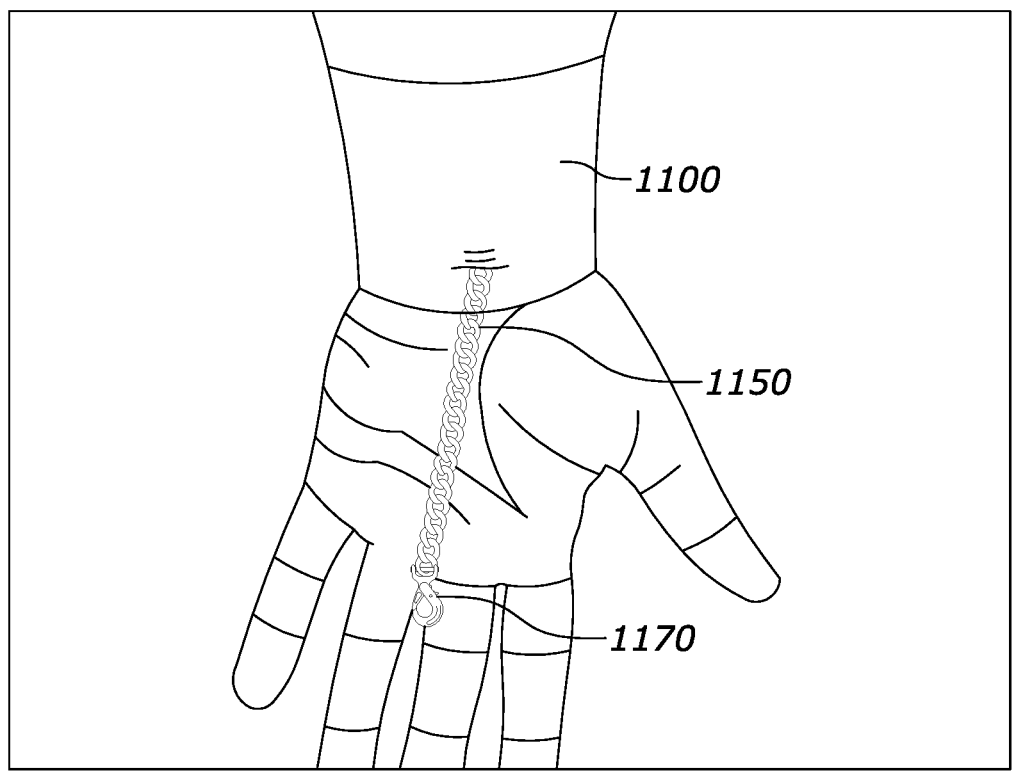
FIG. 12 shows a perspective view of the wrist band and connector chain with the wrist band wrapped around and secured to a person's wrist consistent with present principles.

FIG. 12 shows this band 1100/chain 1150 combination with the band 1100 wrapped around and secured to a person's wrist on the same arm as the finger fracture, sans splint 100, pad 600, and ring 900 for illustration.

Figure 13:
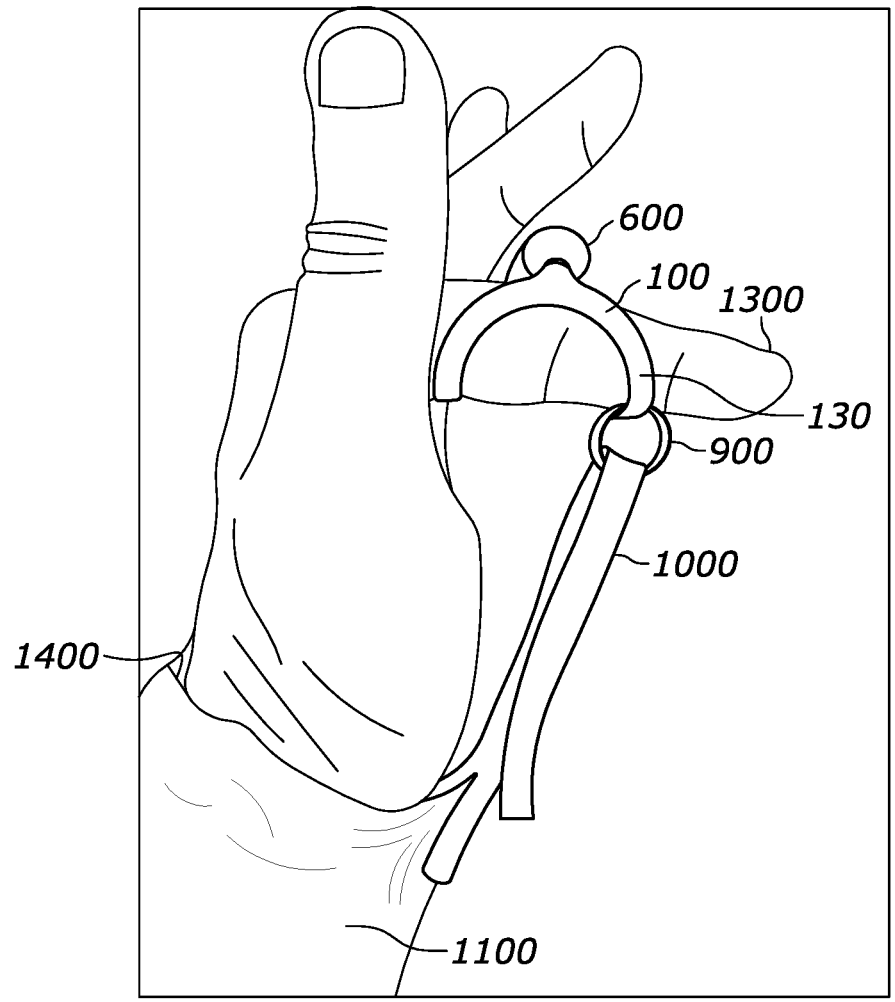
FIG. 13 shows an assembled brace in side view, with this brace including a single splint, a ring, a connector strap, and a wrist band as all engaged with a user to hold a finger at a desired flexion consistent with present principles.
Figure 14:
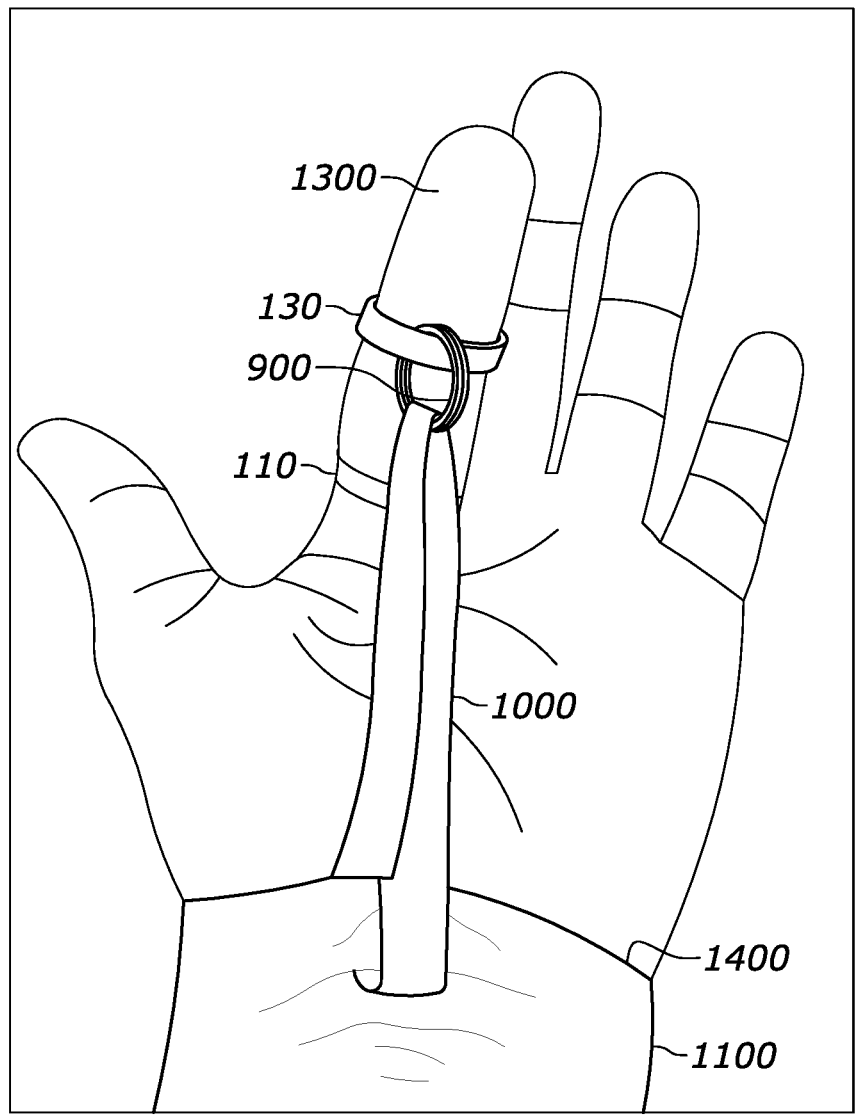
FIG. 14 shows the assembled brace in palmar view consistent with present principles.

Referring now to FIGS. 13 and 14, respective side and palmar views are shown of an assembled brace device with components described above as engaged with a finger 1300 and wrist 1400 on a person's arm. Note that while the ring 900, strap 1000, and wrist band 1100 are shown, alternatives as disclosed above may also be used (e.g., the chain 1150 rather than strap 1000). In any case, it may be appreciated from FIGS. 13 and 14 that the strap 1000 or other connector has been set and fixed at a length to hold the finger 1300 at a desired flexion at the metacarpophalangeal joint and with respect to the hand. In preferred but non-limiting examples, the desired flexion may be ninety degrees in the palmar direction relative to a longitudinal axis of the hand/arm itself, or at least in the range of eighty to one hundred degrees.

Figure 15:
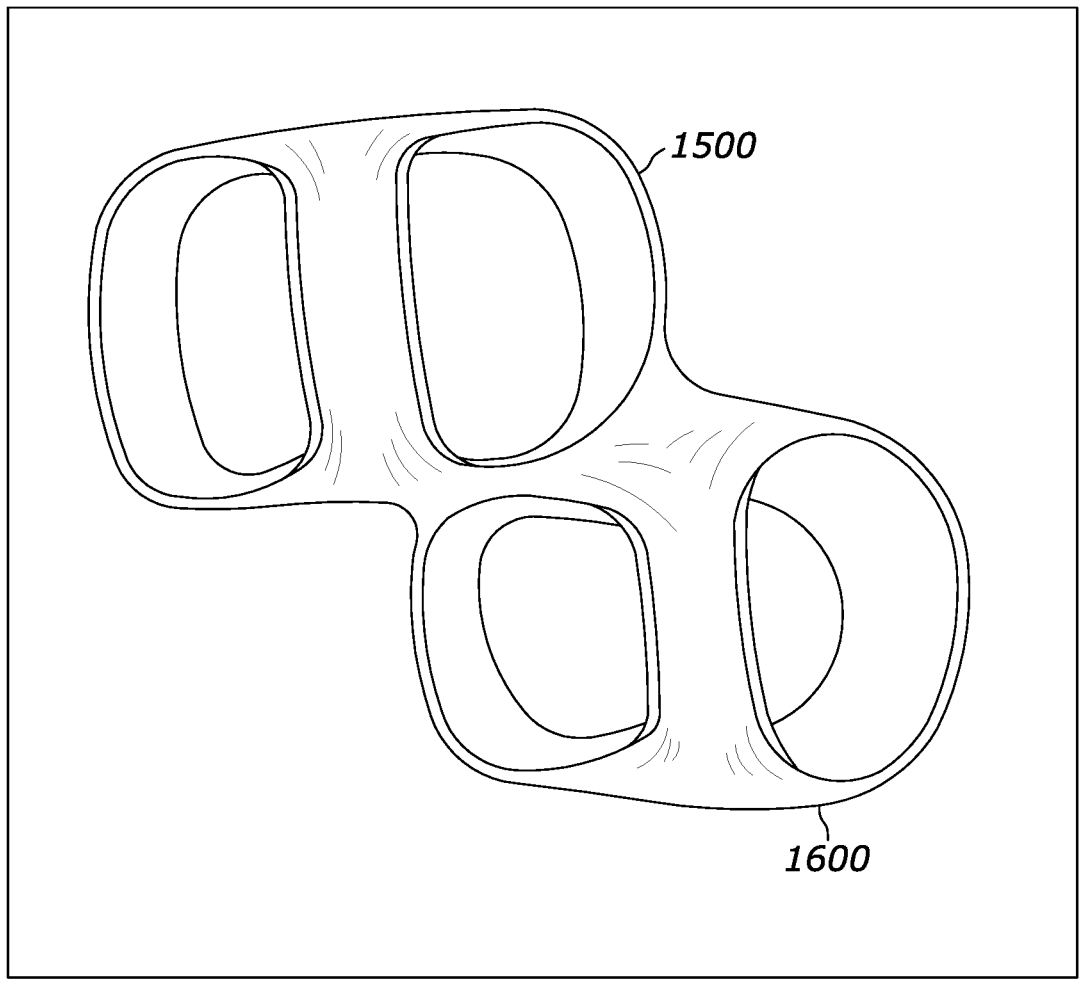
FIG. 15 shows an example two-splint embodiment in top perspective view consistent with present principles.
Figure 16:
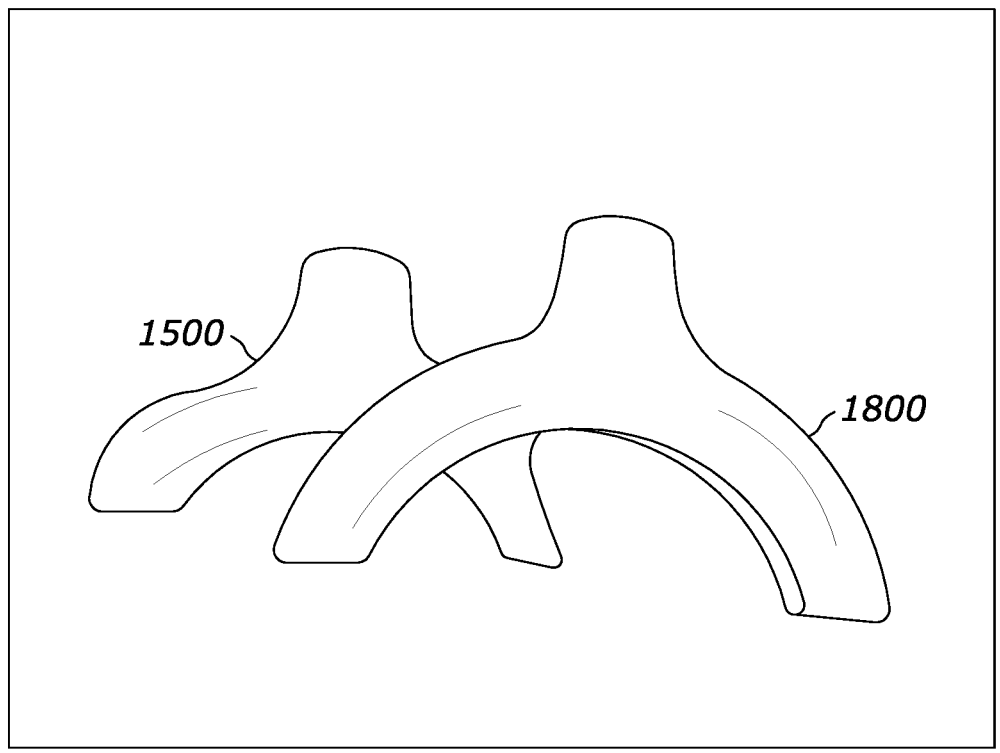
FIG. 16 shows the two-splint embodiment in side elevational view consistent with present principles.
Figure 17:
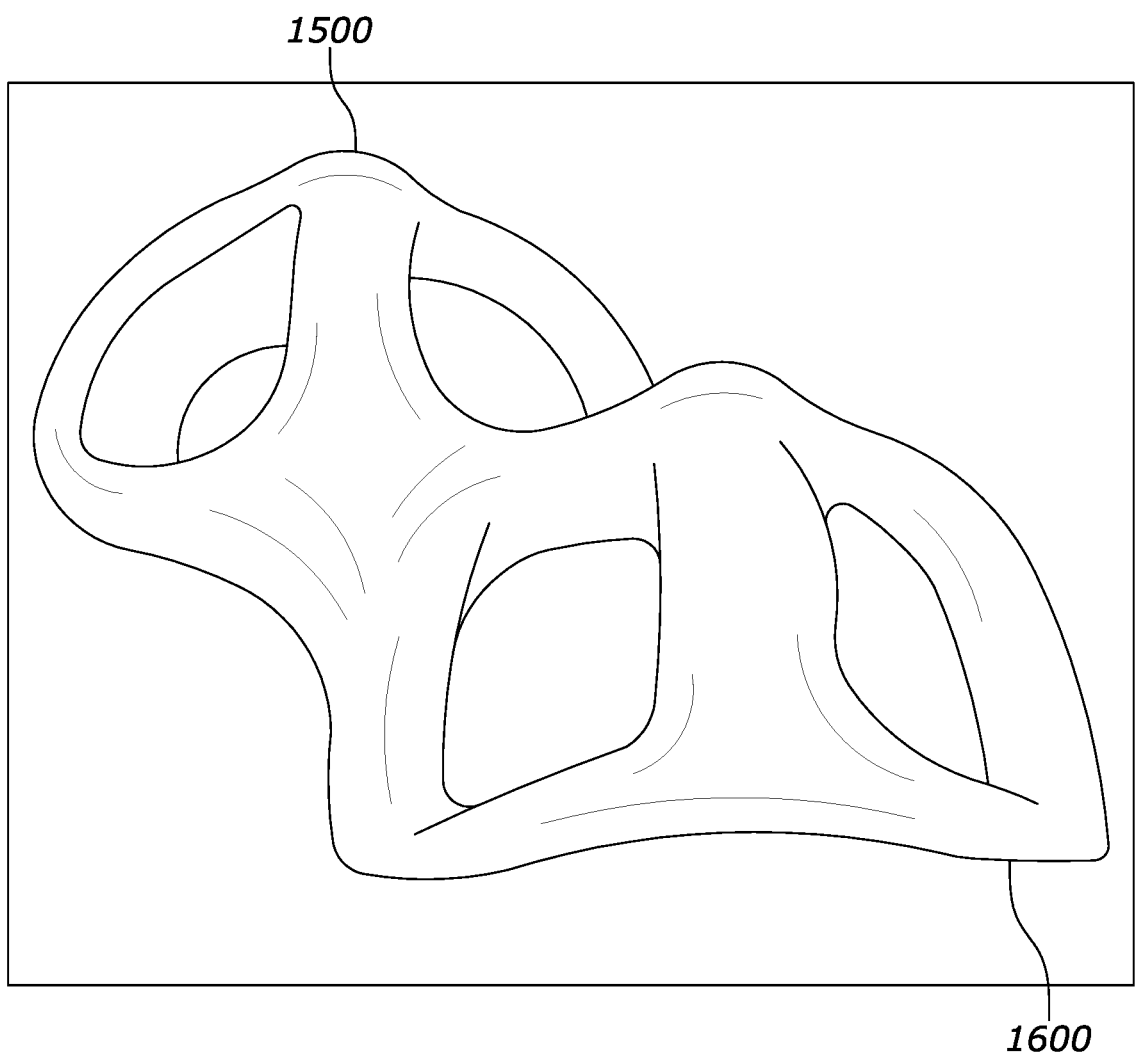
FIG. 17 shows the two-splint embodiment in top/dorsal perspective view consistent with present principles.

Now in cross-reference to FIGS. 15-17, another example splint embodiment is shown consistent with present principles. FIG. 15 shows a top plan view of this embodiment, FIG. 16 shows a side elevational view of this embodiment, and FIG. 17 shows a top perspective view of this embodiment.

According to this embodiment, first and second splints 1500, 1600 are used. Each of the splints 1500, 1600 may be configured the same as the splint 100 described above, save for the splints 1500, 1600 being integral with each other as shown. For example, the splints 1500, 1600 may be molded together or otherwise laterally connected to each other as shown. Thus, for example, a distal arcuate band of the splint 1500 and arcuate side member of the splint 1500 may be molded integrally with a proximal arcuate band of the splint 1600 and arcuate side member of the splint 1600. Note that the distal arcuate band of the splint 1500 and proximal arcuate band of the splint 1600 may be similar to the bands 110, 130 as described above and, as such, may each extend volarly downward to engage a volar area/bottom surface of the respective finger. Also note that the respective side members of the splints 1500, 1600 may be similar to the side members 140, 150 described above.

The splints 1500, 1600 may be configured for respective engagement with adjacent fingers and may therefore have inner heights and widths that vary slightly from each other. Each splint 1500, 1600 may therefore still be configured to contact the respective finger at three spaced-apart locations of the respective finger. In the particular example shown, the splint 1600 is lateral to the splint 1500, with the splint 1600 being offset from the splint 1500 in the proximal-to-distal dimension. However, in another example embodiment, the splint 1600 may not be offset from the splint 1600 in a proximal-to-distal dimension and instead the splints 1500, 1600 may be laterally connected and even with each other in the proximal-to-distal dimension.

Figure 18:
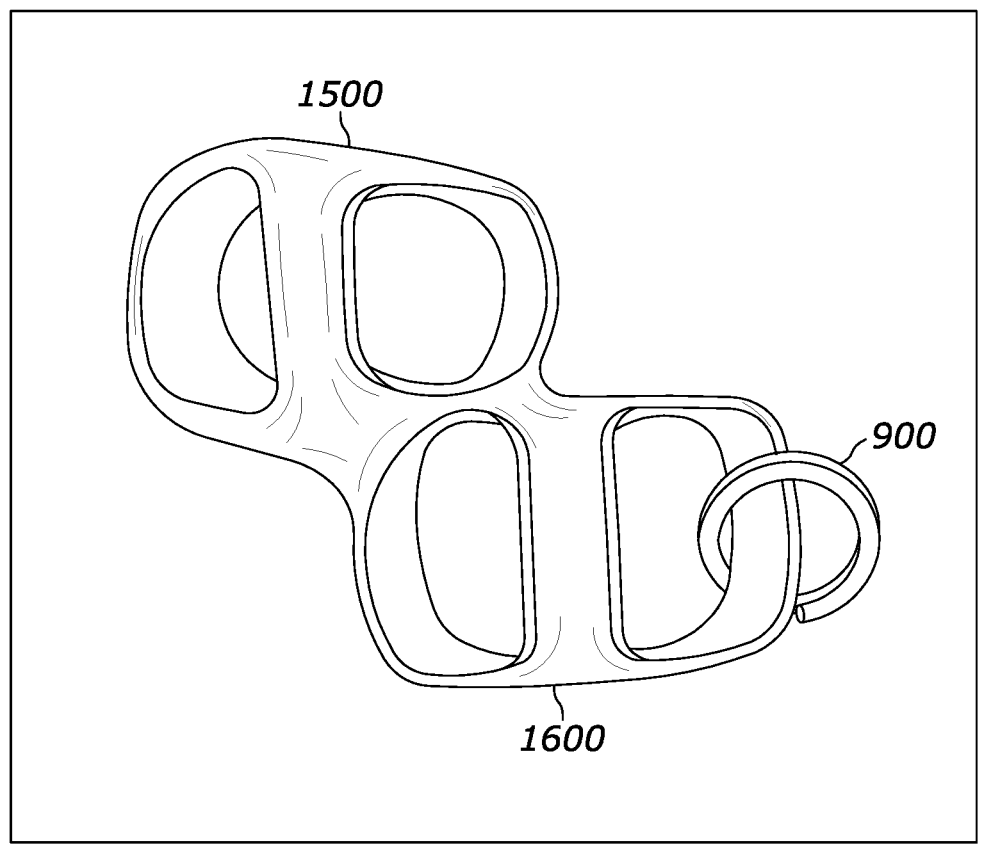
FIG. 18 shows a top perspective view of the two-splint embodiment with a ring coupled to an arcuate distal band thereof consistent with present principles.

FIG. 18 then shows the splints 1500, 1600 with a ring 900 coupled to the splint 1600, with it being assumed per this example that the respective finger to be engaged with the splint 1600 is the one with the fracture being immobilized. Hence, the ring 900 is engaged with a distal arcuate band of the splint 1600. But if the splint 1500 were the one used to engage the fractured finger, the ring 900 might instead be engaged with a distal arcuate band of the splint 1500.

Figure 19:
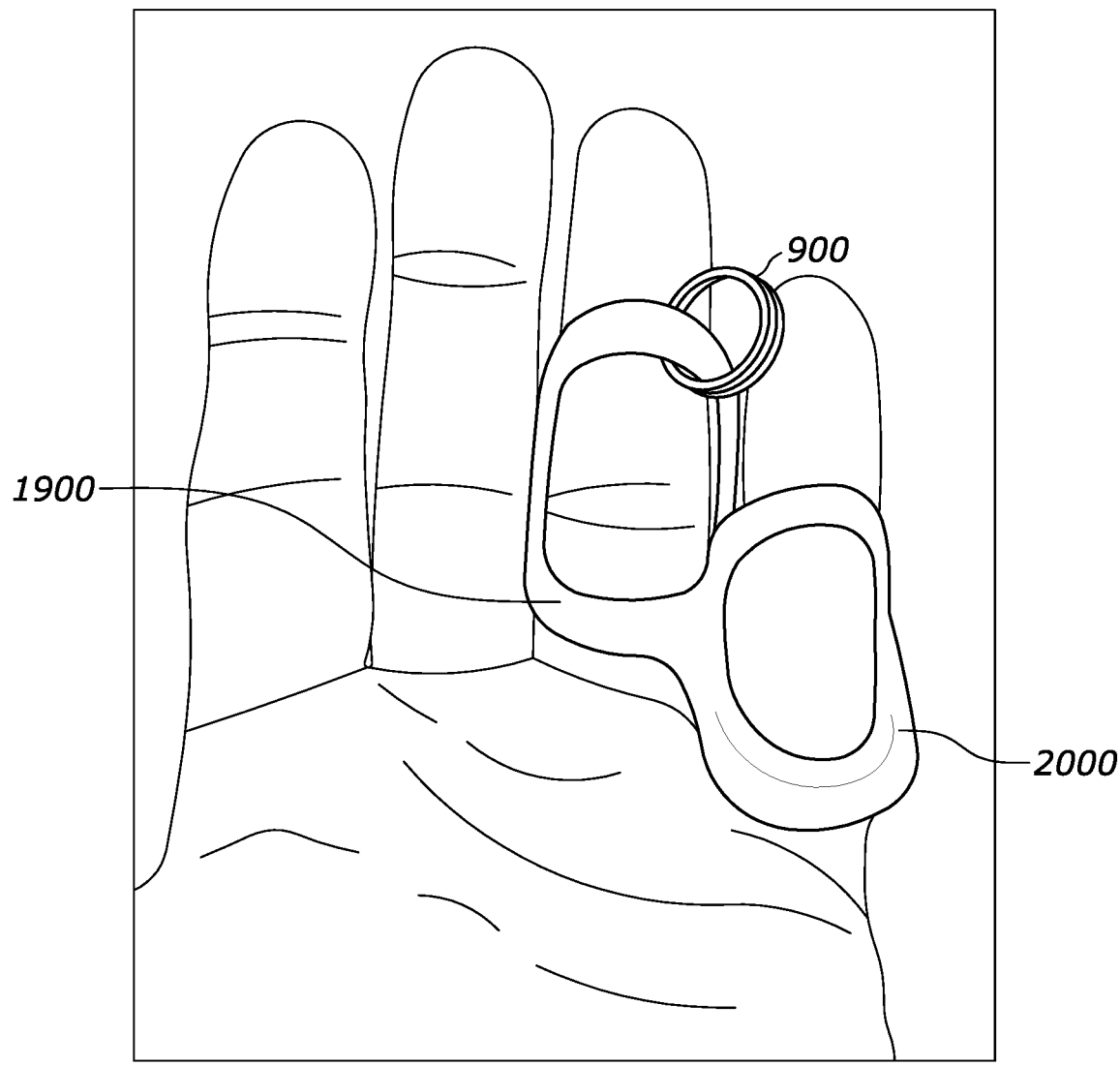
FIG. 19 shows a palmar view of the two-splint embodiment with the ring coupled to an arcuate distal band and with the splint slid onto a person's hand consistent with present principles.
Figure 20:
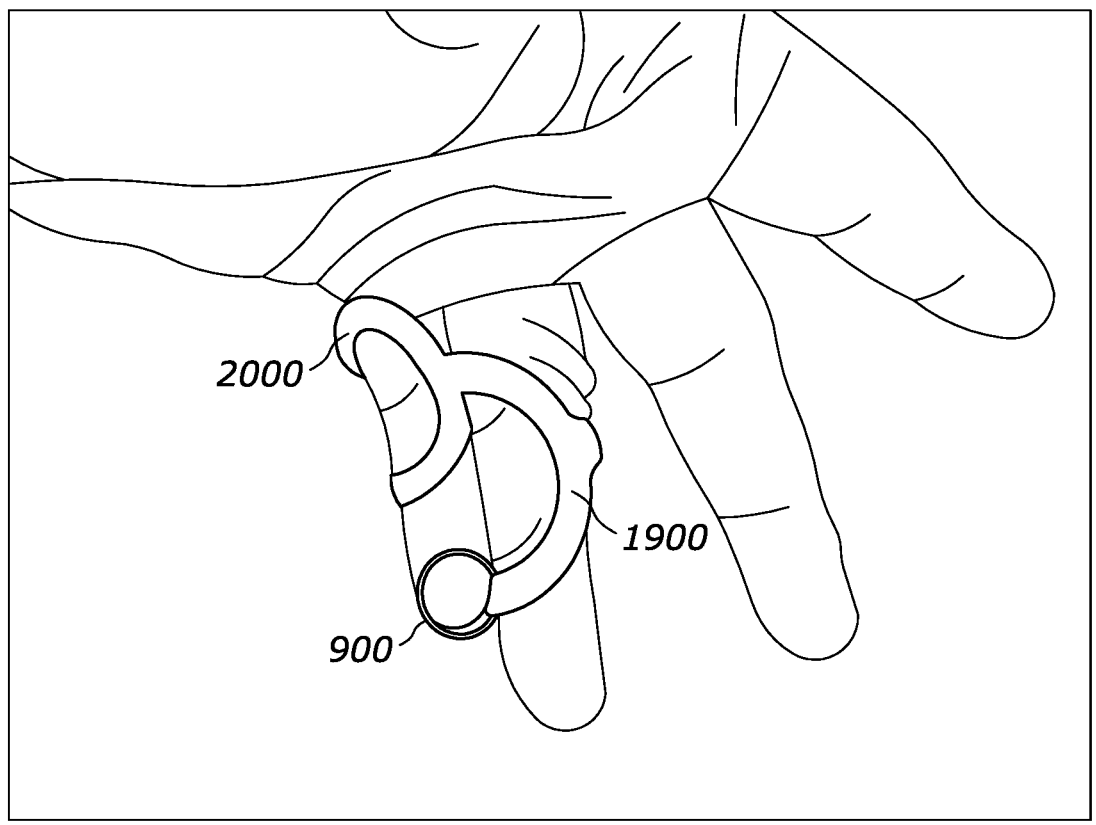
FIG. 20 shows the example of FIG. 19 from a palmar view while two fingers are placed in a desired flexion consistent with present principles.

FIGS. 19 and 20 next show an offset two-splint device as described above, but with splints 1900, 2000 engaged with adjacent fingers on a person's left hand and with the PIP joint of the ring finger being the fractured joint for which immobilization is sought per this example. Specifically, FIG. 19 shows a palmar bottom view of the hand with splints 1900, 2000 engaged with and immobilizing respective PIP joints of the hand, while FIG. 20 shows a palmar perspective view of the same.

Figure 21:
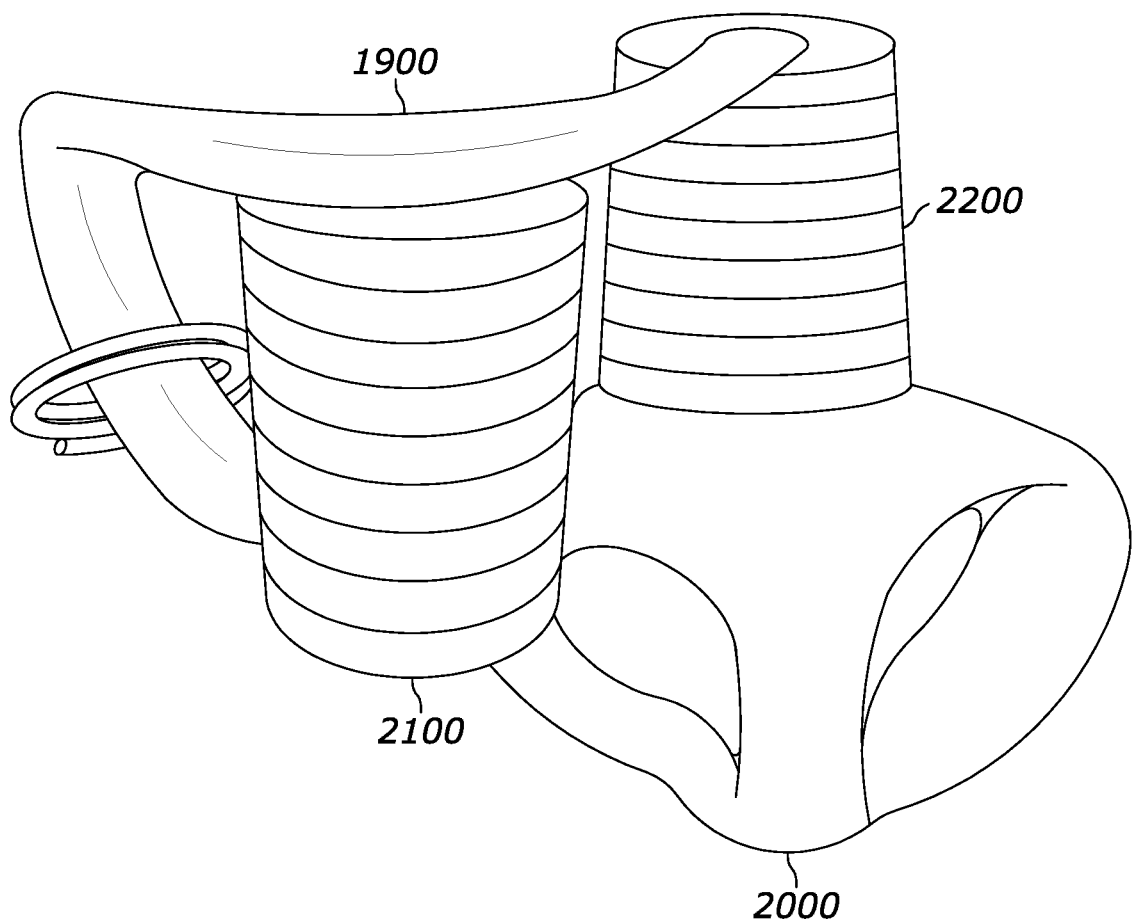
FIG. 21 shows a dorsal perspective view of the two-splint embodiment with foam pads engaged therewith consistent with present principles.
Figure 22:
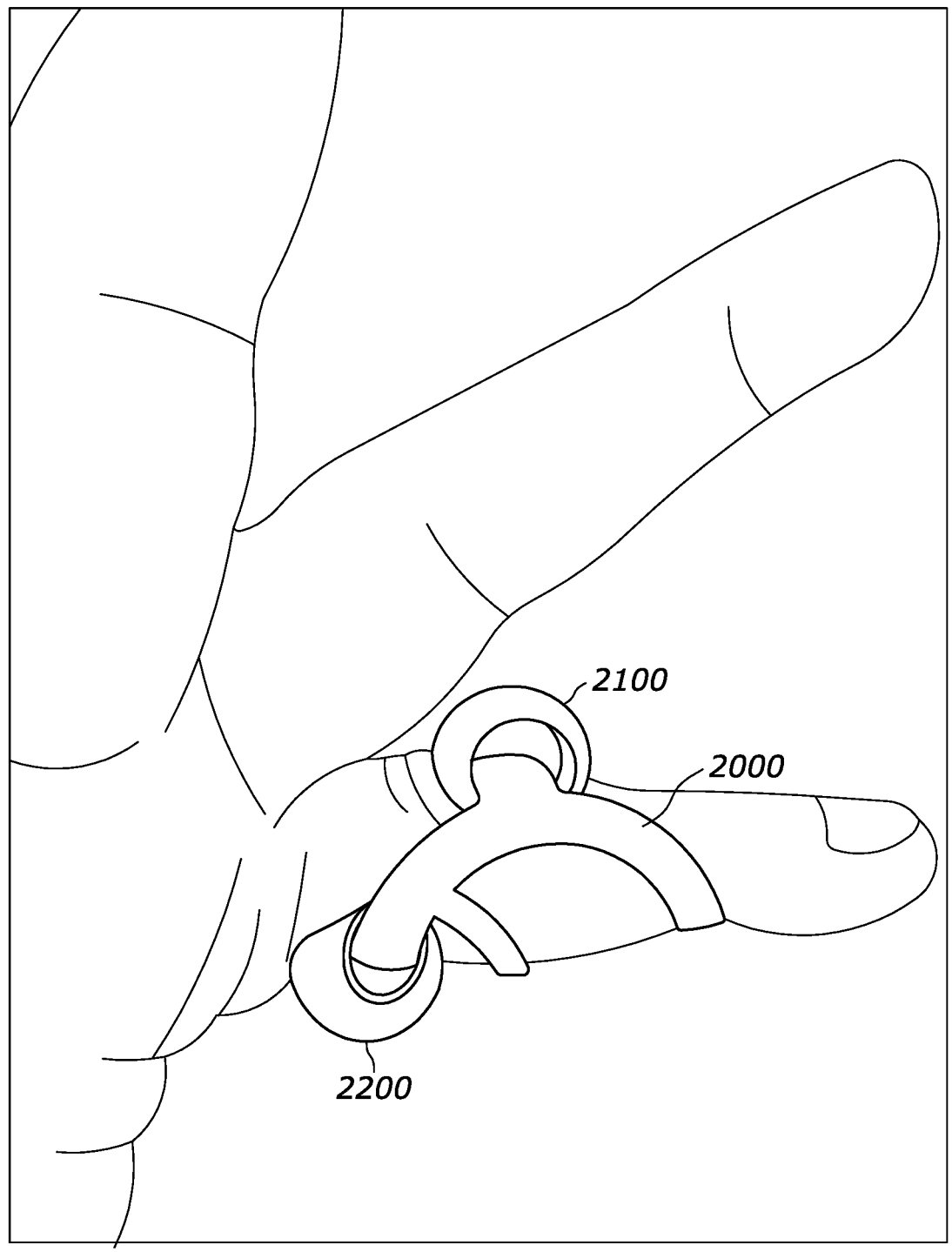
FIG. 22 shows a side elevational view of the two-splint embodiment with foam pads as slid onto the fingers of a person consistent with present principles.

Additionally, if desired a respective foam pad 2100, 2200 as shown in FIGS. 21 and 22 may be engaged with respective arcuate bands of one of the splints 1900, 2000 (the splint that is to immobilize a fractured finger). Each pad 2100, 2200 may be configured similar to the pad 600 as described above. FIG. 21 shows a top perspective view of the two-splint device with foam pads by themselves, and FIG. 22 shows a side elevational view of the two-splint device with foam pads as engaged with a left ring finger and pinkie finger of a person's hand.

As may be appreciated from FIGS. 21 and 22, the pad 2100 has been mechanically engaged with an arcuate band like the band 120 described above that extends dorsally upward to engage a dorsal area/top surface of the respective finger, while the pad 2200 has been mechanically engaged with a proximal arcuate band like one of the bands 110, 130 described above that extends volarly downward to engage a volar area/bottom surface of the same finger. And though not shown in the present example, further note that another foam pad might be engaged with the distal arcuate band extending volarly downward so that a respective pad is engaged with each arcuate, lateral band of the splint 1900. Also if desired, one or more similar foam pads may be engaged with one or more of the arcuate, lateral bands of the splint 2000 as well.

Indeed, all combinations of one pad, two pads, or three pads for each splint are envisioned according to present principles, depending on implementation. For example, one pad may be engaged with any one of the three arcuate bands of the respective splint, two pads may be respectively engaged with any two respective arcuate bands of the same respective splint, or three pads may be respectively engaged with a respective one of each of the three arcuate bands of the respective splint. Also note that this applies to single-splint embodiments as well (such as those described above with reference to FIGS. 1-6) in addition to the two-splint embodiment presently being described. Thus, one, two or three pads may be used for a given splint depending on desired fit and comfort for the particular person using the device, as well as depending on which pad combination results in the respective splint being stabilized in close fit with the respective finger itself (e.g., to prevent jostling or unintended movement of the splint with respect to the finger).

Figure 23:
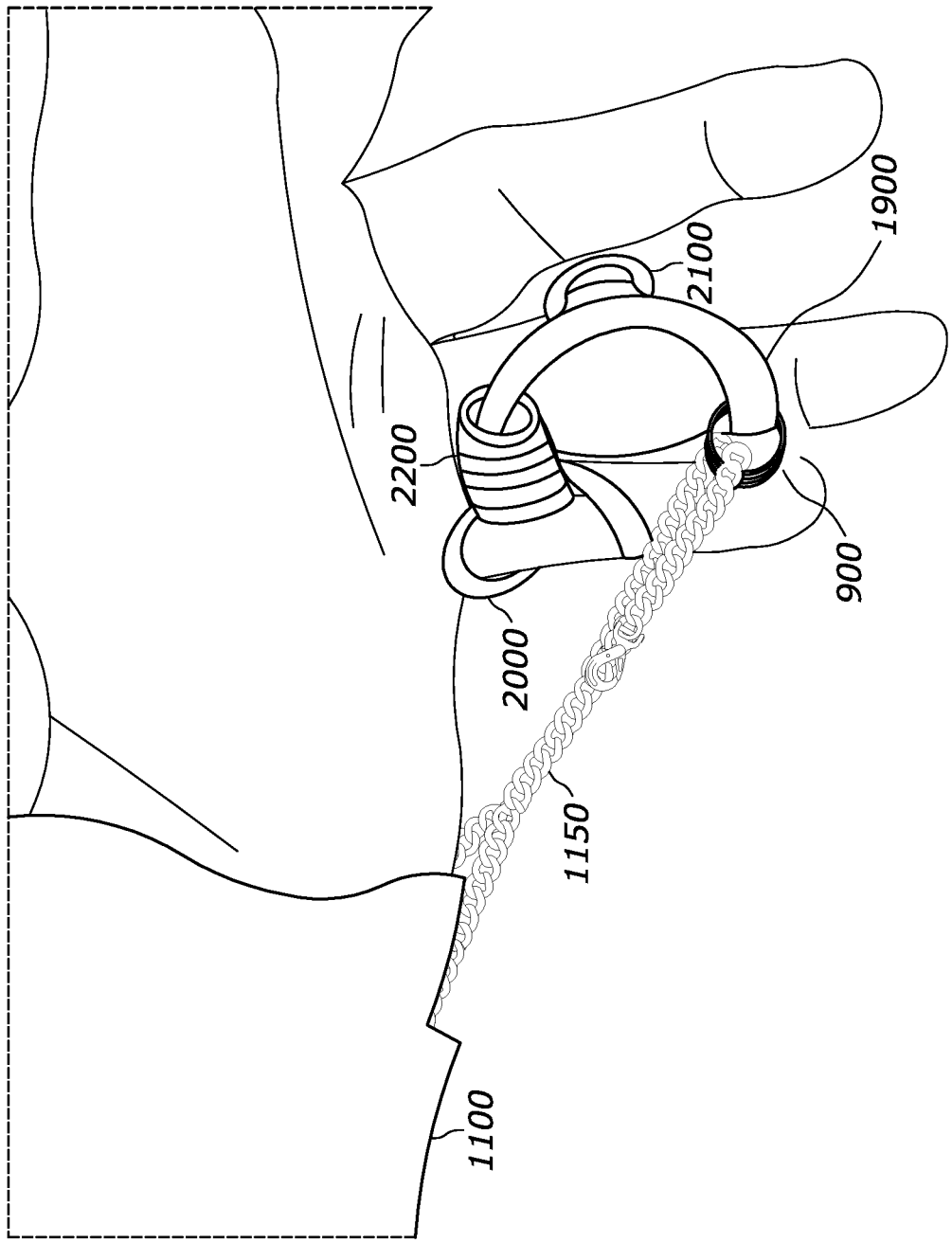
FIG. 23 shows a palmar view of the two-splint embodiment with foam pads and with the assembled brace holding two fingers in desired flexion consistent with present principles.

Now in reference to FIG. 23, it shows a palmar perspective view of an example two-splint brace/device engaged with a left arm of a person. Thus, the band 1100 is wrapped around the left wrist, with the chain 1150 mechanically connecting the band 1100 to the ring 900. The ring 900 itself is engaged with a distal, volarly-extending arcuate band of the splint 1900. The splint 1900 is engaged with a ring finger of the left hand as shown, while the splint 2000 is engaged with a pinkie finger of the left hand. The pads 2200, 2100 are also engaged with the splint 1900, such as via respective slits in the pads 2200, 2100 to accept a respective segment of the splint 1900 to removably and individually engage each foam pad with the splint such that a user can select which foam pad to engage with the splint depending on desired comfort and stabilization levels. It may thus be appreciated that the fractured ring finger is held at a desired flexion at the metacarpophalangeal joint, with again may be ninety degrees extending volarly downward.

Accordingly, it may be appreciated that a one-splint device or two-splint device consistent with present principles may be used for stabilization and correction of finger injuries as well as reduction and stabilization of finger fractures. Each splint may be a three-point finger splint in that each splint may have bands contacting the respective finger at three spaced-apart areas (that are more than respective single geometric points per se)

Thus, in reference to a single-splint device consistent with present principles (such as the splint described above in reference to FIGS. 1-6), the splint may include a single arcuate body, created by injection molding, from a semi rigid material. The splint can be applied over the proximal interphalangeal (PIP) or distal interphalangeal (DIP) joints, treating both flexion and hyperextension deformities and instabilities as well as instabilities and deformities related to arthropathies and fractures.

For example, the splint may be placed over the PIP joint with the center band dorsal for PIP flexion contractures, and/or over the PIP joint with the central band volar for PIP hyperextension deformities (AKA "swan neck" deformities as might be seen in patients with rheumatoid arthritis). These splints can thus be used for different fractures or other conditions of the PIP joint.

Each splint may be sold individually as a single size, or multiple splints of multiple sizes may be sold in a kit/packet. Indeed, this is also true for a two-splint device as well in that multiple different sizes may be sold in a single kit. Either way, the kit may be provided or manufactured by a medical device supplier or other third party such as a drug store, hospital, physician, etc. Thus, rather than a person buying several different splint sizes individually to find the a given splint that is snug but does not cut off blood supply (which could result in death of the finger and need for amputation), a packet of splints of multiple sizes may be purchased. The sizes may vary in width and height as defined by the spaced-apart arcuate bands extending in opposite directions. Length in the proximal-to-distal dimension might also vary among the splint sizes provided in the packet. Accordingly, a snug fit may be realized that provides comfort and/or stability during use of the finger while the splint is engaged thereon.

In addition, recognizing that the finger might go through periods of increased or decreased swelling during healing while the splint is engaged with the finger (e.g., if a tendon is torn or a bone is fractured, the finger would be expected to progressively swell over a period of six days), different pads of different thicknesses may be included in the kit along with the different-sized splints. Thus, pads of a certain thickness may be used that result in stabilization of the splint, but still with the pads being deformable and resilient to accommodate increased or decreased swelling. This prevents the splint from becoming dangerously tight to a point of causing a tourniquet effect. Additionally, owing to the modular nature of the pads, if the swelling increase or decrease is so great that the splint becomes too loose or tight anyway, less-thick or more-thick pads may be exchanged for the ones currently on the splint. Thus, even if the splint was applied at a time of maximal swelling where subsequent decline in swelling would result in splint loosening and therefore loss of splint effectiveness at stabilizing the joint, the kit may still be used to apply different splints of different sizes and/or different pads of different thicknesses that again result of secure, snug fit of the respective splint to stabilize the joint.

Accordingly, in one specific example, one or more slit tubular foam pads may be made available in varying thickness and included in a kit. The pads can be applied to the contact surfaces of the three-point finger splint. By way of example, the tubular foam pads may be offered in a packet having several pads of three different diameters.

Per non-limiting examples below, a contact surface may be or include the portion of the three-point finger splint that laterally extends across the dorsal or palmar side of the finger.

Thus, first a three-point finger splint may be selected so that the fit is slightly loose about the injured finger. Next, respective tubular foam pads may be positioned about one or more of the three contact points of the splint until a snug, comfortable fit is achieved. The foam pads may thus create a more comfortable contact surface to the finger, and the result may be a more-snug fit than can be achieved by use of a three-point finger splint alone. This custom fit may allow much greater stabilization of the affected area with greater comfort and relatively little to no compromise of safety.

The foam pads can also be quickly replaced with a thinner or thicker pad as needed. The slit in each cushion/pad permits the cushion to be positioned about the contact surface and then rotated so the slit is away from the contact surface. For example, if there should be increased swelling of the injured finger, the existing pad can be replaced with a thinner pad; or the pad can be removed entirely. This ability to replace or remove the existing pad can prevent a painful and potentially dangerous overly-tight splint that could cause a tourniquet effect and potential loss of the finger. Conversely, if swelling of the injured finger should decrease, the existing pads can be exchanged for thicker pads, thus maintaining the snug fit and stabilization of the finger.

Before the patient goes to sleep, when there is less conscious awareness of a potential tourniquet effect, the existing pads can be exchanged for thinner pads to decrease the risk of necrosis and need for amputation. Then the thicker pads can be exchanged back after waking from sleep.

Present technology can also be used to treat contractures of the finger joints by adding successively thicker pads to the three pressure points of the contracted joint to maintain constant corrective force while the contracture improves.

Additionally, often-injured fingers often do not conform to the size and shape of a non-injured finger. For example, if a person has a finger deformity from rheumatoid arthritis or osteoarthritis, there is often severe swelling of one joint and gross instability and displacement of the finger in multiple planes. This differential swelling and deformity might otherwise prevent a snug fit of a three-point splint, absent present principles. In addition, the same custom slit tubular pads can be spun laterally to one side or another, affecting a corrective force in the side-to-side plane, not just the flexion extension plane. Thus, while injured fingers can each be unique and each finger on each person has its own shape, deformity and instability, a splint and kit consistent with present principles allows the user to customize the device/brace to their specific finger.

Still further, according to another embodiment, a custom fitting three-point splint can be used to allow reduction (correction of the alignment of the fractured bone) and immobilization of proximal phalanx fractures (and/or proximal phalanx volar plate avulsion fractures). So rather than treating proximal phalanx fractures with buddy-taping (taping the injured finger to the adjacent finger), which does not correct the alignment of the displaced fracture nor does it stabilize the finger in the correct position of 90 degrees flexion at the metacarpophalangeal (MCP) joint, a splint device consistent with present principles may be used. The fracture of the proximal phalanx may be a hyperextension injury from bending a finger back, such as attempting to catch a basketball. The reduction maneuver therefore involves the opposite motion, or flexion of the finger through the MCP. Buddy-taping does not flex the finger through the MCP joint, nor does it immobilized the finger with the MCP flexed.

Accordingly, this embodiment of the custom finger splint may use a velcro wrist strap positioned about the wrist and having an extension for attachment to a ring positioned on the three-point finger splint, as described above. When an injured finger is positioned in the three-point finger splint, this will immobilize the injured finger flexed to a ninety-degree position across the metacarpal phalangeal (MCP) joint. The proximal end of the finger splint acts as a fulcrum, at the apex of the dorsally angulated fracture, such that flexion of the finger affects a reduction of the fracture as the fracture "bends over" the proximal end of the finger splint as the finger is flexed. The finger is then held in this flexed position by attaching the tether from the wrist band. Other iterations can involve passing the tether around the distal part of the splint without use of a ring, or use of a chain instead of a velcro strap. Notably, the finger splint can be constantly and rapidly adjusted as the fractured finger goes through phases of increased swelling and then resolution of swelling. Also, the degree of flexion can be modified to both adjust the alignment of the fracture and accommodate for increased or decreased swelling of the hand and finger. An example ideal position for immobilization is with the MCP flexed at ninety degrees, as this may provide better alignment of the fracture and prevent loss of motion of the MCP joint. The proximal end of the MCP joint has a cam shape, such that the side ligaments can become tight if the MCP joint is immobilized in extension, with permanent loss of ability to flex through the MCP joint. This embodiment immobilizes the finger in flexion through the MCP and allows rapid modification or complete release of the flexion. Temporary complete release of the flexion may be used for activities such as reaching into a pocket, typing on a computer, or washing one's hair. Thus, the entire brace need not be removed to allow such activities, and instead the flexion may simply be released while the splint itself remains fully engaged and supporting the injured joint.

Now according to yet another example embodiment involving a double-splint device such as the one described above in reference to FIGS. 15-23, a brace and non-surgical method are realized for reducing and stabilizing a metacarpal fracture of the ring finger or the little finger of a human hand (e.g., fracture of the metacarpal neck). Medical risks and costs associated with surgical treatment may be avoided. The risk of a permanent loss of MCP flexion resulting from immobilization of the metacarpal phalangeal (MCP) in full extension may also be avoided. The risk of finger necrosis and subsequent amputation from tubular or 2/3 tubular designs causing a tourniquet effect may be avoided. The risk of shear or "degloving" injury from tangential force on the surface of the skin from tubular or 2/3 tubular designs may be avoided. Minimal coverage of the skin of the fingers and no coverage at all of the skin of the hand may allow constant assessment for potential infection and prevent delay in detection of infection that can otherwise occur should the skin of the fingers and/or hand be covered. This may decrease the potential for chronic infections of the extensor tendons or MCP joints which can result in permanent loss of the extensor tendons and/or destruction of the MCP joint. The loss of extensor tendons and MCP joints causes severe loss of hand function.

The fit of the staggered splint may be rapidly modifiable using interchangeable tubular foam pads to adjust for increased or decreased swelling, thus maintaining a snug fit without causing discomfort or placing the finger at risk of pressure or tourniquet necrosis. Additionally, in certain specific examples, no pad may be used for the splint on the finger of the fractured metacarpal, as the axial force combined with the flexion of the MCP reduces the fracture, and instead only pads may be used on the second splint for the healthy finger.

The brace may reduce and stabilize the fractured metacarpal by maintaining the MCP joint of the fractured finger in a ninety-degree flexion while applying an axial force along the length of the finger, through the base of the proximal phalanx, onto the palmar aspect of the metacarpal head on the distal end of the fractured metacarpal. The application and maintenance of this axial force along the length of the finger "reduces" (corrects the alignment) of the fracture and maintains alignment until the fracture heals. The brace stabilizes the "reduced" fracture, preventing motions (rotational, flexion/extension, abduction/adduction) that can cause pain and result in non-union or malunion.

Thus, rather than immobilizing all fingers and wrist in a cast or splint, immobilization can be limited to the fractured finger and the larger adjacent finger so that use of the wrist, thumb, index and either middle or small finger is not inhibited. In various non-limiting examples, a "larger adjacent finger" may be either the ring finger, if the metacarpal fracture is of the fifth metacarpal; or the middle finger, if the metacarpal fracture is of the fourth metacarpal. Additionally, this minimal immobilization of the ring and little finger MCP joints can be rapidly released with the wrist band/adjustable MCP flexion strap.

This embodiment can therefore be used to reduce or correct the metacarpal fracture alignment without placing the finger at risk for tourniquet necrosis or degloving injury. It may also allow constant direct visualization of the entire hand and a majority of the injured finger to allow rapid detection and treatment of infection (indeed this goes for a single-splint embodiment consistent with present principles as well). It may also allow custom fit to the finger using interchangeable tubular pads, decreasing the number of "foundational" splints used for a snug fit and allowing immediate adaptation of the splint in the event of increase or decrease in swelling, thus decreasing risk of finger necrosis and need for amputation.

This embodiment may also allow immediate adjustment or release of the MCP flexion to compensate for swelling of the hand or to allow common activities such as reaching into a pocket, typing on a computer, or washing hair. The brace may include a wrist band/adjustable MCP flexion strap component and a staggered finger splint component.

The splint may thus include two arcuate bodies that each capture a different finger. The two arcuate bodies may be connected in a staggered configuration where two three-point finger splints may be used as possibly, maybe even preferably, fabricated as a single unit. Thus, a "staggered" healthy finger may be offset distally relative to the finger of the fractured metacarpal. It is this offset positioning with the two-splint implementation that provides the proximal axial compressive force along the length of the finger, through the base of the proximal phalanx and onto the palmar side of the metacarpal head of the metacarpal fragment distal to the fracture.

The two-finger splint may thus capture and restrict the movement of each finger, immobilizing both fingers in full extension across the respective PIP joints. Two apertures may be present for each finger to slide through for proper positioning of the component. The palmar aspect of each arcuate band (of each three-point splint) may apply pressure to the palmar aspect of each finger, proximal and distal to the PIP joint. The dorsal aspect of each arcuate band may apply pressure on the dorsal aspect of each PIP joint.

The staggered configuration of the finger splint may therefore create an axial force along the length of the finger of the fractured metacarpal in a direction toward the MCP joint. The fractured finger and larger adjacent finger, inside the staggered splint, may then be then flexed ninety degrees at the MCP joint, resulting in "reduction" and stabilization of the metacarpal fracture. The pathological severe fracture bow may be "reduced" to an anatomic pre-injury mild bow.

This ninety-degree flexed position may be maintained by the use of the wrist cuff with an MCP flexion strap which is preferably adjustable in non-limiting examples. The strap is connected on one end to the palmar side of the wrist cuff and on the other end connected to the palmar side of the staggered finger splint. In one embodiment, the strap may be a small link chain that is connected to a ring which is positioned about the palmar aspect of an arcuate band of the staggered splint (e.g., as shown in FIG. 23). This connection may result in secured flexion of the MCP joints. The velcro may allow for rapid release of the strap or modification of the length of the strap, thus allowing immediate adjustment of the degree of MCP flexion (as may be needed in patients with severe swelling, with initial minimal flexion and progressive flexion as swelling subsides) or temporary complete release of flexion (as may be required for multiple activities of daily living such as reaching into a pocket, typing on a computer, or washing one's hair).

Other embodiments may involve use of clips or chains and hooking or connecting the chain at various points to the other respective brace components to achieve different degrees of MCP flexion.

Other embodiments may involve the use of modular velcro pads that can be connected to the skin side of the wrist cuff to decrease irritability from the proximal edge related to traction force from the MCP flexion strap.

The splints can be offered in several "off the shelf" sizes and the proper selected size may be slightly loose so that the cushioned tubular foam pads can be attached. The two-finger, staggered connection, arcuate splint is then slid over the finger of the fractured metacarpal and the adjacent larger finger.

The tubular foam pads may be provided in a variety of varying diameters. Each foam pad may have a slit along its longitudinal access so that the foam pad can be positioned about a respective palmar aspect or dorsal aspect of each arcuate band so a tubular foam pad will be positioned about the six total contact points of the two staggered three-point splints, thereby creating a modular custom fit. The availability of tubular foam pads of varying diameter may thus decrease the number of sizes of splints otherwise manufactured or purchased for achieving a custom fit. Further, if the swelling across the person's finger changes, the foam pads can be changed as necessary. For example, if swelling dissipates, the tubular pads on the splint can be replaced with pads having a larger diameter.

This well-padded snug fit may hold the fingers in full extension through the PIP joints while being snug enough to "capture" each finger such that the staggered relationship between the two arcuate components creates a significant longitudinal force along the length of the finger of the fractured metacarpal. This may be achieved without causing a tourniquet effect, without causing a shear/degloving stress to the skin, and/or without covering the skin of the finger or the hand so as to allow constant visualization of the skin for potential infection.

If the finger should swell, thicker tubular pads can be exchanged for thinner tubular pads, or the splint can be exchanged for a larger splint, thus maintaining a snug fit with maximal comfort and safety.

The normal anatomy of the metacarpal shaft is of an arch, apex dorsal. Due to this arch, when there is axial pressure on the distal end of the metacarpal without flexion of the MCP, the apex dorsal fracture deformity will increase. Thus, an objective of a physician may be to decrease this apex dorsal deformity and straighten or restore the mild apex dorsal arch of the metacarpal. This can be achieved through flexion of the MCP to ninety degrees so that the axial force from the finger is applied to the palmar side of the head of the metacarpal and not the distal end of the head of the metacarpal. The result may be an upward or dorsally directed force on the distal end of the fractured metacarpal, and "reduction" of the fracture. A counter-force may be created by the soft tissue connections between the metacarpal shafts. As the distal fragment of the fractured metacarpal is pushed dorsally, the soft tissues may hold the shaft in place causing a downward or palmar counter force that results in reduction of the fracture. It is for this reason that no direct pressure or downward force is needed on the back side of the hand. Thus, a dorsal pad or force over the fracture site (that might be unnecessary and potentially dangerous in that it could cause pressure sores over the thin skin on the back of the hand and obstruct direct visualization of the hand necessary for rapid recognition of infection) can be avoided.

Accordingly, a reduction brace consistent with present principles can maintain the proper set position of the fractured metacarpal for correct restoration of the mild apex dorsal arch.

With the component parts of the reduction brace described above, a method for reducing and immobilizing a metacarpal fracture of the ring or little finger of a human hand may be appreciated to include the steps of positioning a velcro cuff with attached MCP flexion strap around the wrist of the affected hand, with/without attachment of modular velcro pads on the palmar proximal edge of the cuff. The method may then include positioning a staggered two-finger splint component about the finger of the fractured metacarpal (e.g., ring or little) and the adjacent larger finger, where correct position may be for the dorsal components of the splint to be over the PIP joints of each finger. The method may then include assessing the two-finger splint for comfort and snugness of fit. If the splint is too loose, slit tubular foam pads can be applied to any or all of the six points of contact of the splint with the two fingers. Flexion of the metacarpophalangeal joints of the fractured metacarpal and adjacent non-fractured metacarpal to ninety degrees may be performed (e.g., if possible) and less flexion may be used if there is severe swelling. The method may then include passing the MCP flexion strap through the ring on the palmar side of the staggered splint, attaching the strap back to itself with a velcro surface. The strap can be progressively pulled through more, creating more MCP flexion, as swelling decreases, or released slightly, creating less MCP flexion if swelling increases.

The finger splint size and tubular pad applications can be used to create a modular custom fit and adapt for increased or decreased swelling of the fingers, so as to maintain a snug fit without placing the fingers at risk for necrosis.

Accordingly, one embodiment of the brace allows for application of an extra-large slit tubular foam pad to the proximal-most bar (of the finger of the fractured metacarpal) of the staggered finger splint so that direct pressure can be applied to the palmar aspect of the palmar surface of the distal fractured metacarpal, as opposed to only axial force from the base of the proximal phalanx onto the palmar aspect of the metacarpal head of the fractured metacarpal.

Another embodiment of the brace may allow adjustment of the diameter or length of the finger splint components to allow fine tuning of the fit (e.g., by placing different components of each splint on tracks that can then lock the components into place with respect to each other).

Another embodiment of the brace may permit separate finger splints to be removably connected to each other through a snap fit or other connection to allow ease of reduction or release of pressure.

Yet another embodiment of the brace may allow changes to the relative position of each finger splint, for example, further or less staggering between the two finger splints, or a change in the angle between the two splints (e.g., using one or more tracks that couple the two splints).

Therefore, according to various examples, a reduction brace may include a two-finger component, a wrist band, and an adjustable MCP flexion strap. The MCP flexion strap can take various forms. In one embodiment, the MCP flexion strap may be a chain connected to the wrist band and two-finger component.

Thus, reduction of the most common metacarpal fracture, which is for the 5th metacarpal (commonly referred to as the little finger metacarpal) may be realized. The procedure may be the same if the fourth metacarpal or ring finger were fractured. The only difference might be that the size of the two-finger component may be larger to accommodate the ring finger and adjacent middle finger. Both sizes of the two-finger component may be included in a single kit, if desired.

A velcro wrist band with attached adjustable MCP flexion strap may include a velcro wrist strap with areas on the skin side of the volar proximal edge for potential attachment of further padding, and a long strap, with a velcro surface, attached to the palmar side of the wrist band.

The two-finger component may include a pair of arcuate annular bodies integrated with one another. A common wall may define a portion of the arcuate bodies, which may be in a staggered relationship to one another. The two-finger component may be created by an injection molded process or other process, and may be semi-rigid. Each arcuate body portion may have a pair of apertures for a respective finger to be slidably received and immobilized across the PIP joint of the fractured finger and larger adjacent finger. Finger contact areas may contact the palmar side of the finger of the fractured metacarpal proximally and distally to the PIP joint (e.g., as shown generally in FIG. 19) and there may be a contact area that makes contact with the dorsal surface of the PIP joint on the finger of the fractured metacarpal as illustrated in FIG. 20. Similarly, contact areas are on each side of the PIP joint on the palmar surface of the adjacent larger finger and contact area may be on the dorsal surface of the PIP joint. The configuration of each arcuate body can thus have a pair of elliptical apertures which can be seen in FIG. 17.

The assembled reduction brace illustrated in FIG. 23 may be assembled by first applying the wrist band with attached adjustable MCP flexion strap around the wrist of the injured hand. The wrist band may be applied with a dorsal velcro surface.

A connector ring may be positioned around the two-finger component. The connector ring may be used to connect the MCP flexion strap to the wrist band.

Care may be taken to have the band in such position that the adjustable MCP flexion strap may be on the palmar side of the wrist. The finger of the fractured metacarpal and the adjacent larger finger may then be slid into the arcuate bodies of the two-finger splint component to the desired position. Once the fingers are positioned within the two-finger component, because of the staggered position of the two fingers, an axial compressive force is applied and maintained along the length of the finger of the fractured metacarpal.

However, when the fingers held in the two-finger component are flexed to a ninety-degree position across the MCP joint, the compressive force contact surface may be changed from the distal end of the metacarpal head to the palmar side of the metacarpal head, pushing the head of the fractured metacarpal dorsally, decreasing the apex dorsal deformity. The flexed position of ninety degrees may be maintained by attaching the adjustable MCP flexion strap to an eyelet on the palmar side of the two-finger splint.

An additional force can be utilized to enhance reduction of the fractured metacarpal if optional tubular foam pads are incorporated. The force may be applied by engagement of both tubular foam pads when the fingers are flexed ninety degrees across the MCP joint.

Therefore, a brace may be provided for reducing and immobilizing a metacarpal fracture of either the little finger or ring finger of a human hand and using the adjacent larger finger for reduction and stabilization. The brace may include a two-finger component including a pair of arcuate annular bodies, each sharing a common wall where the arcuate bodies are in a staggered relation to one another, each arcuate body having a pair of apertures sized to slidably receive a respective finger, immobilize the finger in full extension, where each annular body has separate finger contact areas for positioning: on opposing sides of a respective proximal interphalangeal joint for contact with the palmar surface, and upon the dorsal side of a respective proximal interphalangeal joint; and where the two-finger component maintains an axial compressive force to the finger of the injured metacarpal in a direction toward the metacarpophalangeal joint.

Tubular foam pads can be provided for placement over the six contact points of the two-finger component, increasing comfort and reducing the variety of sizes of two-finger components that might be tried to achieve custom fit. The tubular foam pads may have a longitudinal slit for placement of each foam pad about the contact point. This may also permit the foam pads to be replaced if necessary if the swelling of the finger increases or decreases.

The adjustable MCP flexion strap component may be passed through the eyelet component and attached to itself allowing for varying degrees of MCP flexion and rapid reversible release of MCP flexion without need for removal of the brace.

An adjustable MCP flexion strap component with a long velcro surface may be used to allow varying amounts of the strap to be passed through the eyelet, allowing varying amounts of flexion of the MCP, rapid change in the degree of flexion of the MCP, and rapid reversible release of the MCP flexion for brief periods to allow activities of daily living (such as reaching into a pocket, typing on a computer, or washing one's hair) without need for removal of the brace.

Accordingly, in one aspect a brace for reducing and immobilizing a metacarpal fracture of either the little finger or ring finger of a human hand and using the adjacent larger finger for reduction and stabilization may include a two-finger component. The two-finger component may include a pair of arcuate annular bodies sharing a common wall where the arcuate bodies are in a staggered relation to one another, each arcuate body having a pair of apertures sized to slidably receive a respective finger and immobilize the finger about its proximal interphalangeal joint, where each annular body has separate finger contact areas for positioning: a) on opposing sides of a respective proximal interphalangeal joint for contact with the palmar surface, and, b) upon the dorsal side of a respective proximal interphalangeal joint; and where the two-finger component maintains an axial longitudinal force along the finger of the fractured metacarpal in a direction toward the metacarpophalangeal joint.

Also in one aspect, a brace for reducing and immobilizing a metacarpal fracture of either the little finger or ring finger of a human hand and using the adjacent larger finger for reduction and stabilization may include a wrist band component. The wrist band component may have an attached adjustable MCP flexion strap that includes a velcro wrist band with velcro connection on the dorsal aspect of the wrist band and a long velcro covered strap attached to the palmar side of the band. The wrist band can accept modular pads, attached by velcro to pad all areas, including the distal skin side edge of the wrist band, thus increasing comfort and decreasing risk of pressure sores in the area where the adjustable MCP flexion strap is applying traction. The brace may also include an eyelet component that may be incorporated in the palmar side of the two-finger component such that the adjustable MCP flexion strap can be passed through the eyelet and connected to its own velcro surface, holding the MCP in a flexed position.

Further, in one aspect a finger and hand splint system may be realized, where the system may be provided as a kit. This kit may be designed to treat several common finger and hand injuries and conditions, including the potential improved alignment of the two most-common fractures of the hand (the fracture of the little finger metacarpal (Boxer's Fracture) and the fracture of the base of the finger). The same kit may also be used to treat deformities of the DIP and PIP joints related to trauma (e.g., fracture, ligament, or tendon injuries), or rheumatoid or osteo arthropathies. The same kit is able to treat flexion or extension contractures of the PIP and DIP joints and avulsion injuries of the extensor tendons (both distal insertion into the base of the distal phalanx and the central slip insertion into the base of the middle phalanx). The modular pads may allow a custom, safe and comfortable fit to the individual person's finger (as all fingers may be unique). The ability to rapidly interchange the pads may allow rapid accommodation of increased or decreased swelling, and/or can be used to apply progressive pressure when treating contractures.

Additionally, the wrist cuff and tether may allow easy, rapid release or adjustment of the MCP flexion to achieve the best desired fracture reduction and accommodate to increased or decreased swelling.

All conditions of the hand may be initially evaluated by a physician, with application of this splint system and explanation of the correct position of the splint being provided along with the risks and benefits associated with use of splints.

Accordingly, some of the many hand conditions that can be treated with this system include the following.

Mallet Finger—this may be a detachment of the extensor tendon from the base of the bone on the end of one's finger. The result is that the tip of the finger flexes down and cannot be extended. The physician can decide best treatment, surgery or splinting. If splinting is recommended, the finger may be placed into a splint device as described herein and pads may be applied to extend the finger through the far (DIP) joint.

Boutonniere Injury—this may be a detachment of the extensor tendon from the base of the bone in the mid finger, such that the finger flexes at this joint and extends at the end joint. The physician can decide best treatment, surgery then splinting or just splinting. If splinting is recommended, the finger may be placed into a splint device as described herein and pads may be applied to extend the finger through the near (PIP joint).

Fracture of the base of the finger—the finger bone closest to the hand, the proximal phalanx, can be treated with surgery and splinting or just splinting. If the physician recommends splinting, the finger may be placed in a splint device as described herein and pads may be applied for a snug but comfortable fit. A cuff may then be placed around the wrist and the tether from the cuff may be attached to the splint to hold the finger flexed and the knuckle (MCP joint). The amount of flexion can be modified to achieve best alignment of the fracture and most comfort during periods of swelling.

Fractures of the near joint (PIP joint) of the finger—as with all conditions, the physician can recommend best treatment. If use of a splint is recommended, a splint device as described herein can be placed across the PIP joint. If the finger is displaced to one side or the other, a splint device as described herein can be spun to one side or the other and pads applied, to affect correction of the deformity.

Fractures of the metacarpal neck (e.g., Boxer's Fracture)—If splinting is recommended, there may be two treatment options. As a first option, less-displaced fractures can be treated with a single finger splint as described above, which may be placed over the fractured finger, buddy taped to the adjacent finger, and attached to the wrist cuff tether. This may allow for X-rays to be taken in the splint to assess fracture alignment. As a second option, more severely-displaced fractures can be treated with the staggered two-splint system described above. A kit consistent with present principles may be provided with one or more two-splint components for right and left hands (e.g., with right hand or left hand being marked on the exterior surface of the splint if desired). The splint may be placed over the finger or the broken metacarpal and the adjacent larger finger. Pads may be applied to create a snug but comfortable fit, and the wrist cuff tether may then be attached to hold the knuckle (MCP) flexed. Additional padding can be placed on the palm end of the splint to increase the reduction force.

Finger deformities related to osteoarthritis and rheumatoid arthritis—each person's finger deformity may be unique to them and can be stabilized and partially realigned with use of a finger splint system consistent with present principles. The splint may be placed over the deformed finger and the splint may be slid up the finger and spun to the side until the middle of the splint is at the apex of the deformity. Pads may then be applied to create gentle corrective pressure.

Accordingly, in one specific example a finger splint kit consistent with present principles may include four base sizes of splints (single and/or double-splints) with attached connection ring(s). Also included may be three baggies of slit tubular foam pads, color-coded for diameter. For example, thin pads may be color-coded in yellow, medium (thicker) pads may be color-coded in red, and thick (thickest) pads may be color-coded in blue. The kit may also include a wrist cuff with attached tether.

In addition, that kit or an accessory/companion metacarpal brace kit may include four base sizes of right hand and left hand staggered splints. Also included may be three baggies of slit tubular foam pads, color-coded for diameter (e.g., again with thin pads color-coded in yellow, medium (thicker) pads may be color-coded in red, and thick (thickest) pads may be color-coded in blue). A wrist cuff with attached tether may also be included.

According to another example aspect, a three-point splint may be used consistent with present principles, where the splint involves a single arcuate body, created by injection molding, from a semi-rigid material. The splint can be applied over the PIP or DIP joints, treating both flexion and hyperextension deformities and instabilities. For example, the splint may be placed over the PIP joint with the center band dorsal for PIP flexion contractures and over the PIP joint with the central band volar for PIP hyperextension deformities. These splints can be used for fractures of the PIP joint.

The splints can be purchased as a single size, or in a packet of multiple sizes. Present principles provide comfort and stability during use of the finger. In addition, if the finger should have increased or decreased swelling, the splint may be adjusted so as to not become dangerously tight or loose to a point of losing effectiveness at stabilizing the joint.

Present principles also recognize that pathologic fingers often do not have a shape comparable to a healthy finger. For example, a person with an arthritic PIP joint may have severe swelling of the PIP joint but no swelling proximal or distal. Here, slit tubular foam pads of varying thickness can be applied to the contact surfaces of the three contact point finger splint. The consumer may buy a packet with three sizes, for example. Each splint may then be applied until a fit is found that is slightly loose. The slit foam pads may then be applied to any or all of the three contact points of the splint until there is a snug comfortable fit. The foam pads may create a more comfortable surface, and a more-snug fit. The foam pads may be interchanged quickly as desired. If there should be increased swelling, a thicker pad can be exchanged for a thinner pad, or the pad can be removed entirely, thus preventing a painful and potentially dangerous overly tight splint that could cause a tourniquet effect and potential loss of the finger. If swelling should decrease, the pads can be exchanged for thicker pads, thus maintaining the snug fit and stabilization of the finger.

At night time, when there is less conscious awareness of a potential tourniquet effect, the thicker tubular pads can be exchanged for thinner pads to decrease the risk of necrosis and need for amputation.

Present technology can also be used to treat contractures of the finger joints by adding successively thicker pads to the pressure point on the apex of the contracted joint.

Yet another iteration of a finger splint and strap system consistent with present principles may be used for fractures of the base of the proximal phalanx. A common orthopedic injury is the fracture of the base of the proximal phalanx of the finger. The most common deformity is angulation of the fracture, apex volar (palmar) or bending of the finger dorsally or back. Thus, a device/brace consistent with present principles may use a splint as described herein and add a connection ring on the palmar aspect of the finger splint, and use a wrist band with adjustable flexion strap to hold the injured finger flexed through the MCP joint. This may not require immobilization of the non-injured fingers, or wrist, and thus causes fewer limitations to activities of daily living. The extension fracture deformity is corrected by flexing the finger through the MCP joint, over the proximal end of the three-point splint. This corrected or "reduced" fracture is then held in the appropriate ninety degree of flexion through the MCP joint with the wrist band and adjustable strap.

The pads on the splint can be interchanged as the swelling of the fractured finger increases and decreases, and the flexion of the injured finger relative to the palm can be instantly modified or temporarily released and reconnected to allow response to increased swelling of the injured finger and hand and to allow brief activities of daily living such as reaching into a pocket, typing, or washing one's hair.

The splint and strap also allow less bulk to enable better-quality X-rays with the splint still in place.

Another iteration may involve two splints attached side to side (e.g., in a non-staggered fashion), thus affecting a buddy tape type immobilization, and to have a flexion strap connected to one of both of the finger splints.

Thus, a device/system consistent with present principles may be versatile in that it can correct tendon injuries in both the distal and middle phalanx of the finger, a bone break in the proximal metacarpal of the finger, and a lateral deformity in a finger because of arthritis (e.g., by putting a single-splint device on sideways), without unduly limiting use of the entire hand. Methods of manufacturing, providing, instructing placement, and/or fitting onto a patient of the devices disclosed herein are also included.

Also consistent with present principles, two different kits might be provided in some implementations. A "standard" kit may be used for finger fractures, where this kit may include four base three-point splints, three baggies of thin, medium and thick slit tubular pads, a velcro wrist strap, and a tether with connection ring (and/or the tether can simply be passed around the distal aspect of the splint).

The second kit may be a metacarpal kit. It may have four base two-splint combinations, staggered, for the right hand. It may also have four base two-splint combinations, staggered, for the left hand. The second kit may also include three baggies of slit tubular pad, a velcro wrist strap, and a tether with connection ring.

If desired, a "master" kit might also be provided (e.g., to emergency rooms) that would be a combination of both of these two kits.

Figure 24:
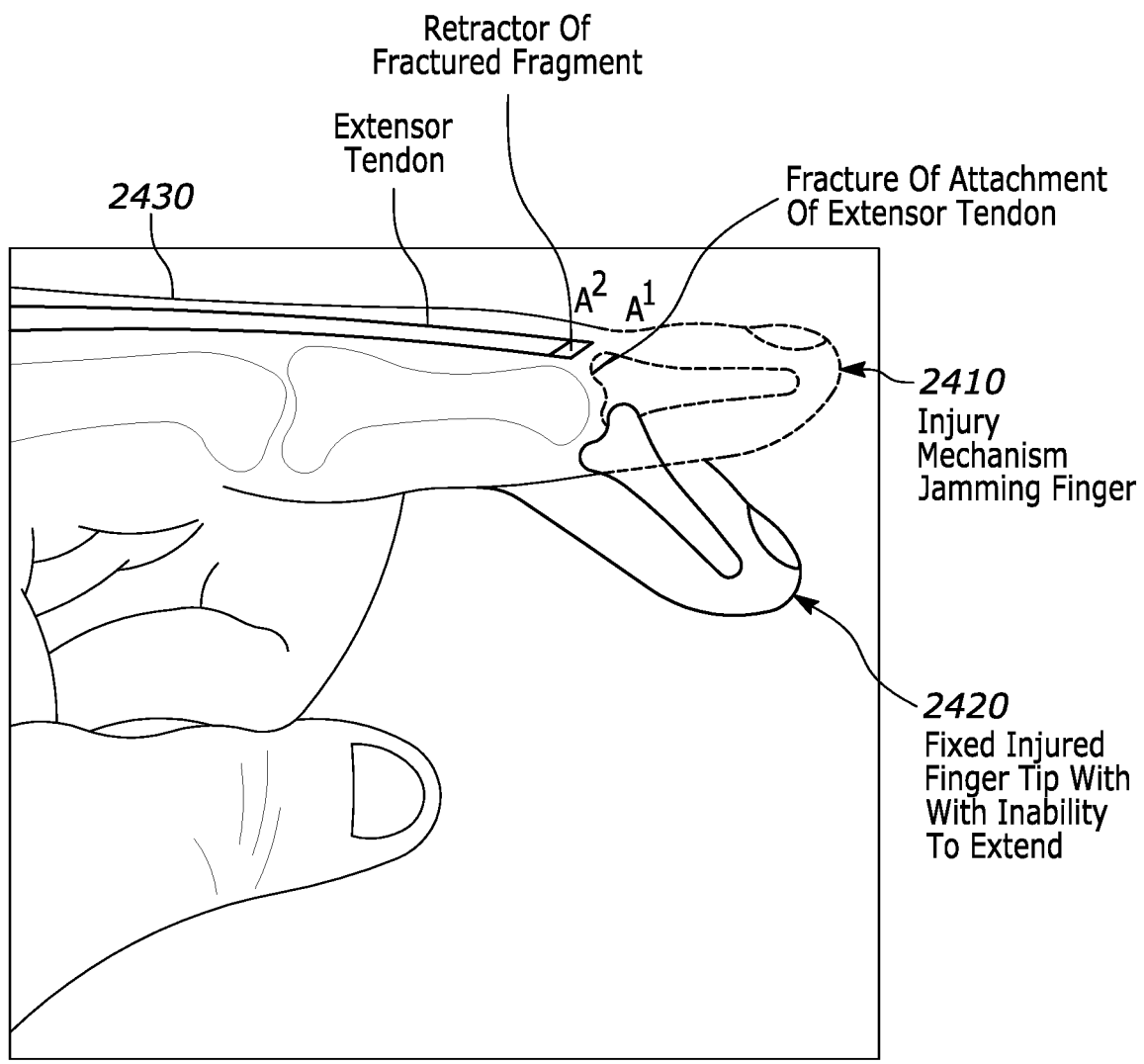
FIG. 24 shows a mallet finger injury mechanism/anatomy in side elevational view.

Now in reference to FIG. 24, this figure shows a mallet finger injury mechanism/anatomy. As may be appreciated from this figure, there has been refraction of the fractured fragment ($A^2$) of the extensor tendon 2400, and fracture of attachment of the extensor tendon ($A^1$). Arrow 2410 indicates a direction of the injury/mechanism jamming the finger. A flexed injured finger tip 2420 with inability to extend is also shown, with the tip 2420 forming part of a finger 2430.

Figure 25:
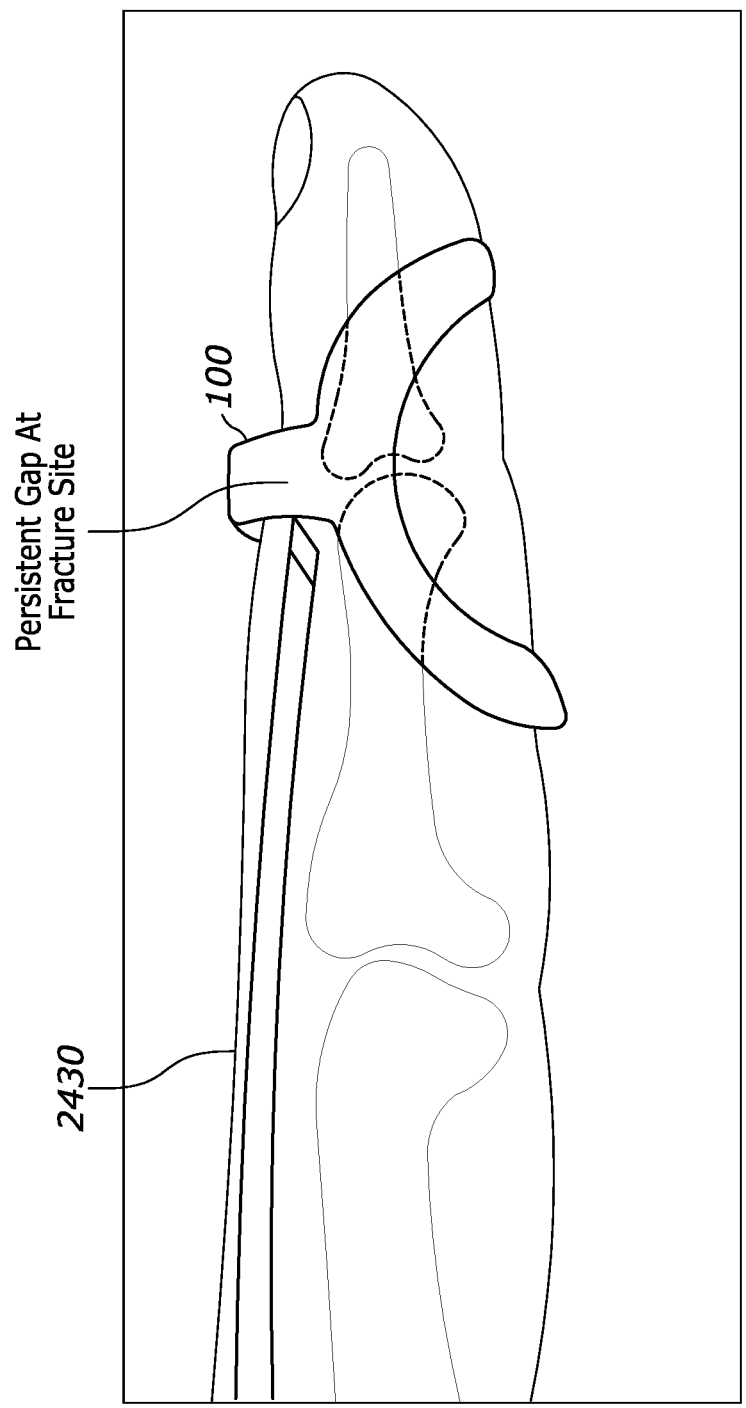
FIG. 25 shows a side elevational view a splint 100 consistent with present principles as disposed on the finger of FIG. 24.

FIG. 25 then shows a splint 100 consistent with present principles as disposed on the finger 2430. This helps some with fracture reduction, however there may be a persistent gap between the finger 2430 and splint 100 at the fracture site. Put another way, use of the splint 100 alone may result in non-union of the fracture from the persistent gap due to retraction of the tendon and fragment of the bone.

Figure 26:
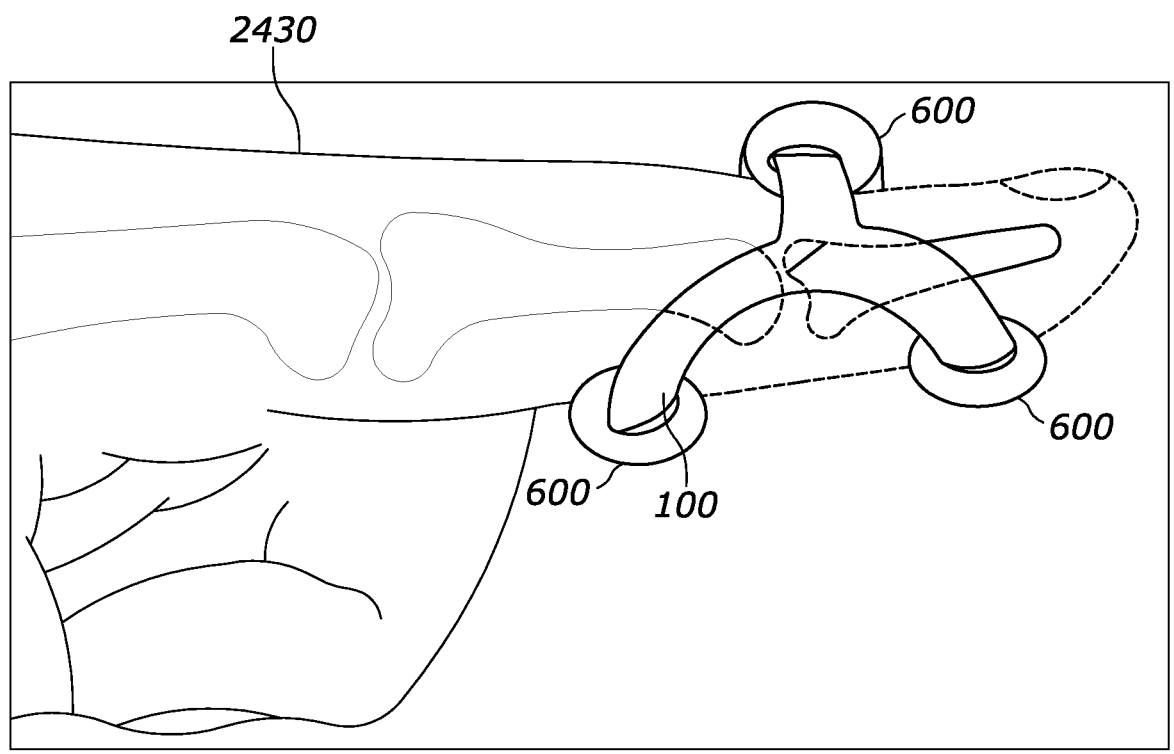
FIG. 26 shows tubular pads being used with the same finger consistent with present principles for enhanced fit and fracture reduction.

Accordingly, FIG. 26 demonstrates improvement over FIG. 25 in that pads 600 as described above have been placed on the bands 110-130 of the splint 100, reducing or eliminating the persistent gap. Use a kit consistent with present principles may therefore allow hyperextension of the DIP (distal interphalangeal joint), thus bringing the site of the fracture to the retracted fragment, allowing it to heal.

Figure 27:
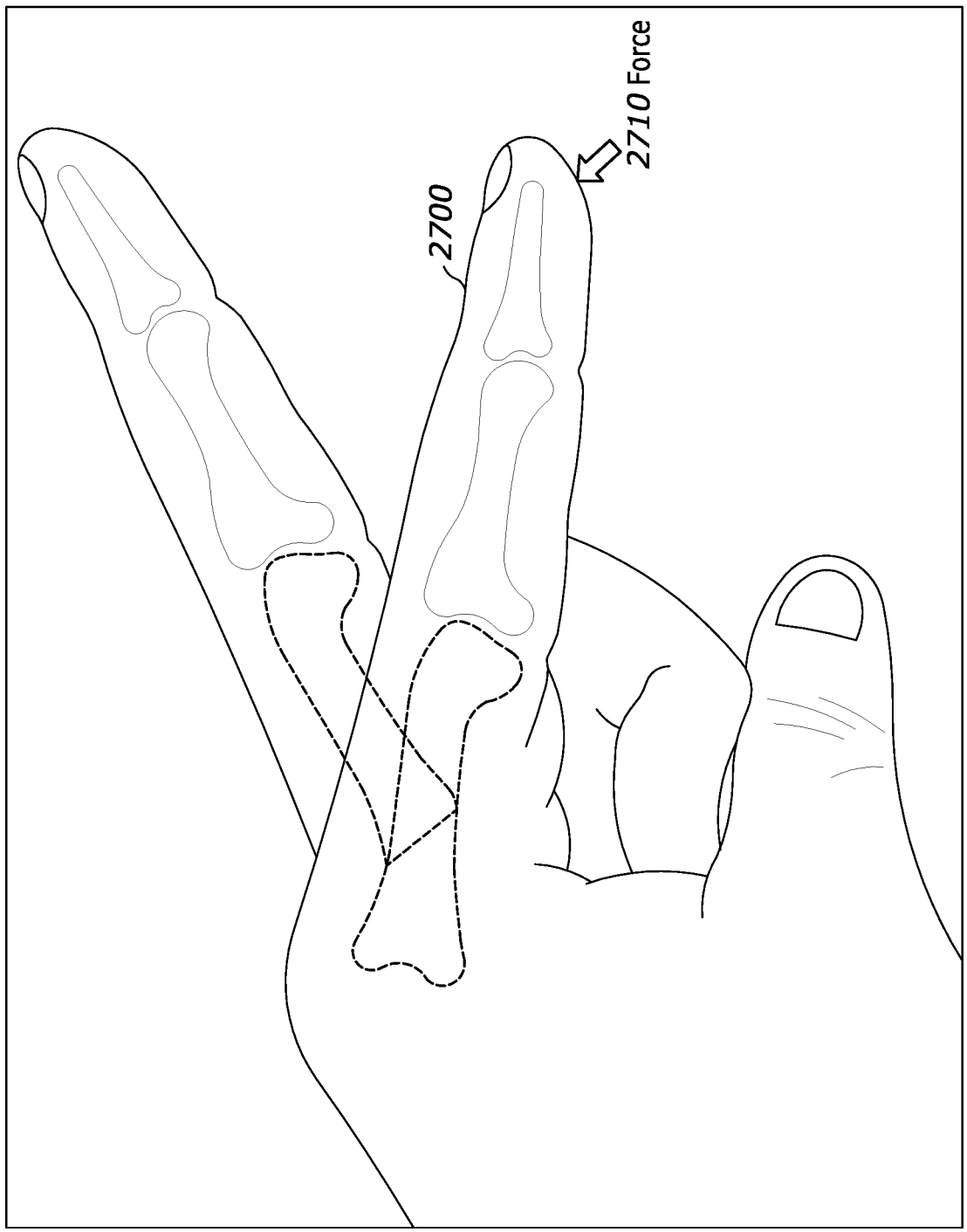
FIG. 27 demonstrates is a proximal phalanx hyperextension fracture in side elevational view consistent with present principles.

FIG. 27 demonstrates another example fracture that might occur to an index finger 2700 based on force from a palmer-to-dorsal direction 2710 as shown. Here, the fracture is a proximal phalanx hyperextension fracture.

Figure 28:
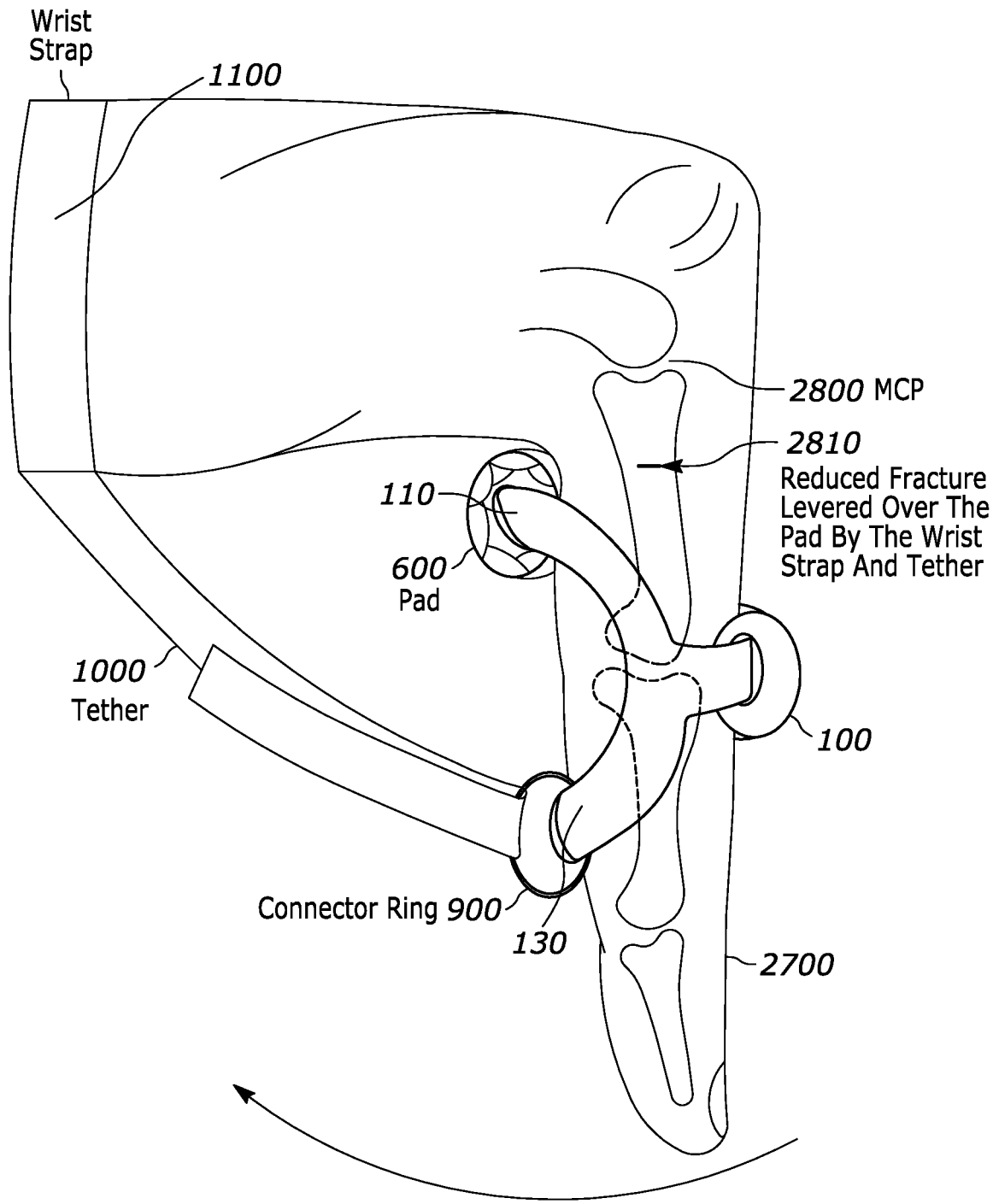
FIG. 28 shows a side elevational view of a splint and pads with wrist strap and tether correcting the alignment of a fracture and immobilizing the fracture in the correct position for healing consistent with present principles.

FIG. 28 then shows a splint 100 with a pads 600 on the palmar proximate band 110 of the splint 100, with the distal band 130 being coupled to a ring 900, which itself is coupled to a tether 1000, itself coupled to a wrist band 1100 for wearing by the patient. Use of the pad 600 on the palmar proximate band 110 thus results in a reduced fracture 2810, with the fracture 2810 levered via the metacarpophalangeal (MCP) joint 2800 over the pad 600 as held in place by the wrist strap 1100 and tether 1000. Accordingly, application of a kit/device consistent with present principles may allow flexion of the fracture over the fulcrum of the pad 600 placed under the proximal end of the splint (e.g., band 110). This helps correct the alignment of the fracture 2810 and immobilizes the fracture 2810 in the correct position for healing.

Figure 29A:
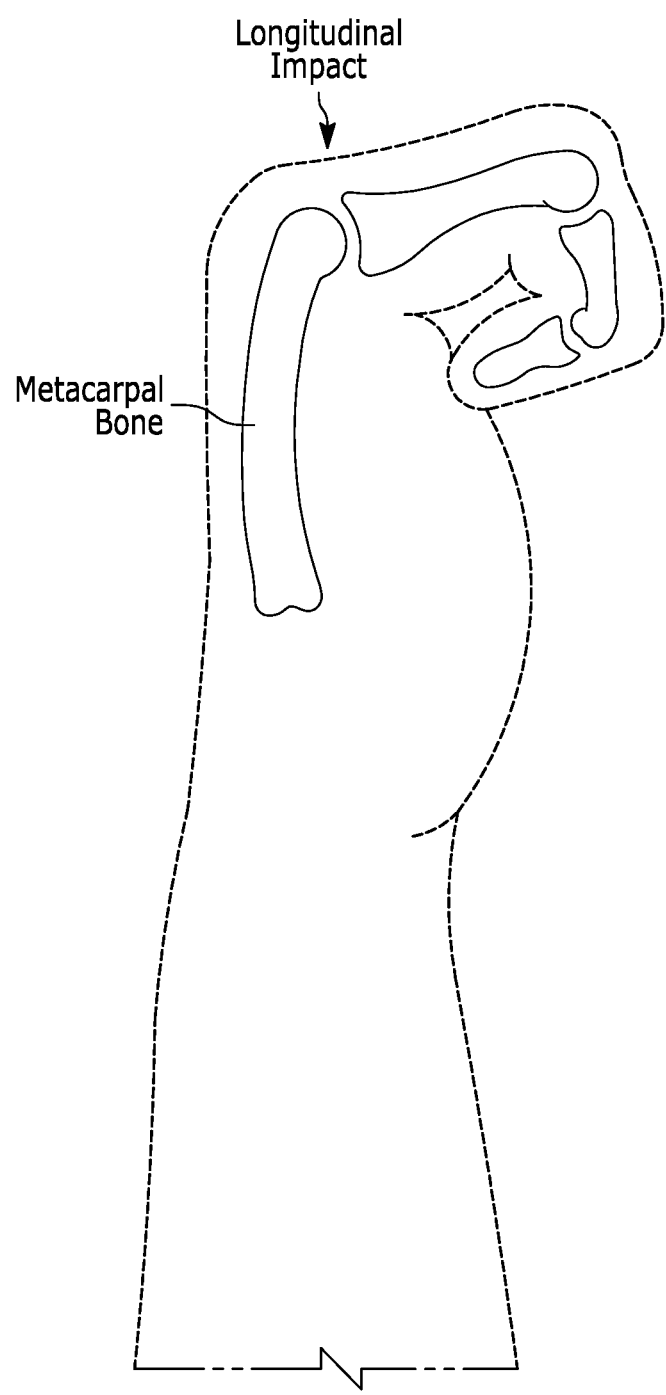
FIGS. 29A and B show a mechanism of injury for a metacarpal neck fracture (e.g., Boxer's Fracture)
Figure 29B:
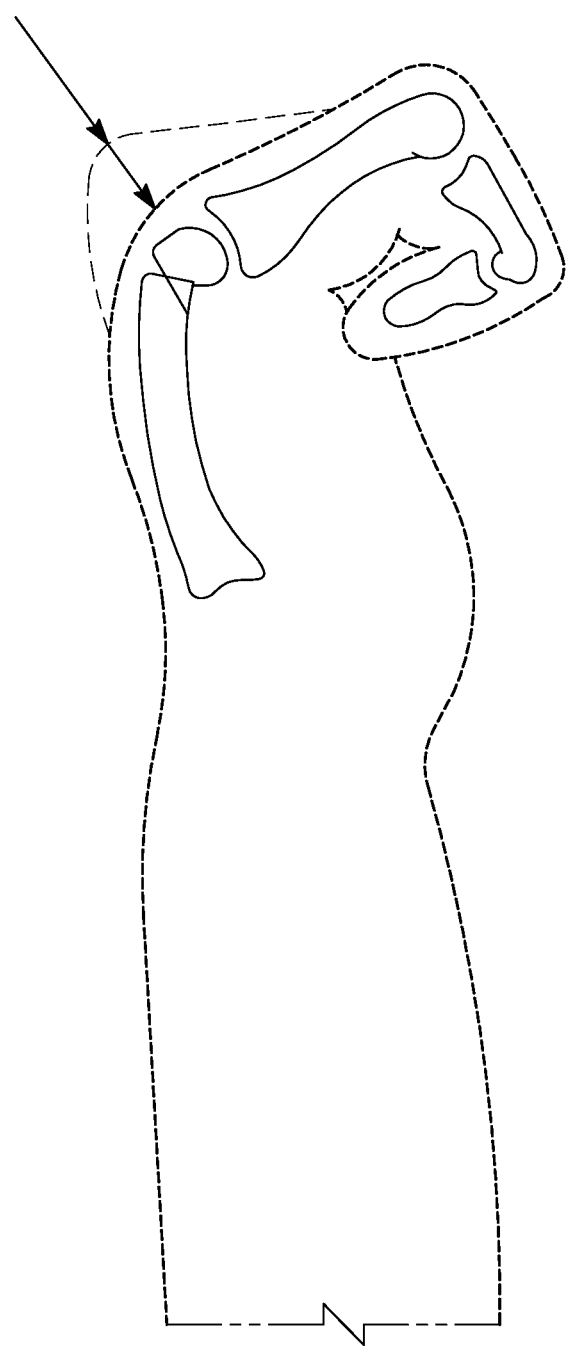

FIGS. 29A and B show a mechanism of injury for a metacarpal neck fracture (e.g., Boxer's Fracture).

Figure 30A:
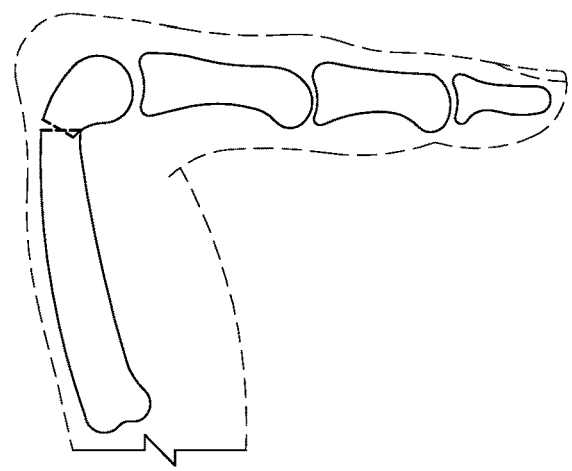
FIGS. 30A-C show an intraoperative reduction maneuver involving flexion of the MCP (metacarpophalangeal) joint and upward pressure along the length of the finger onto the palmar side of the metacarpal head, thus showing the correction of the alignment as one progresses from FIG. 30A to FIG. 30C.
Figure 30B:
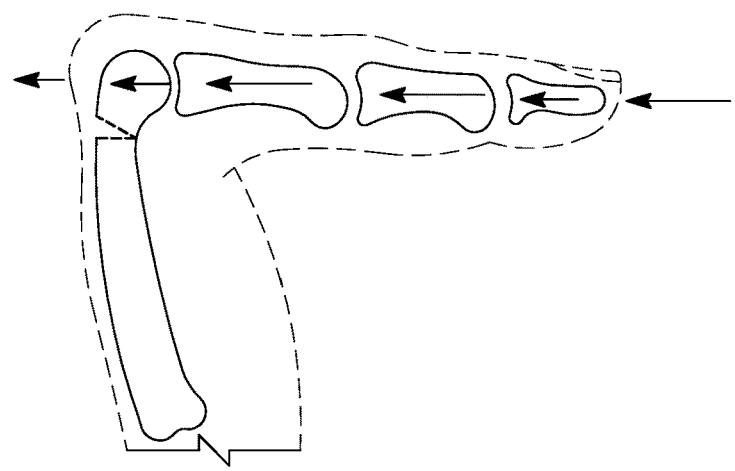
Figure 30C:
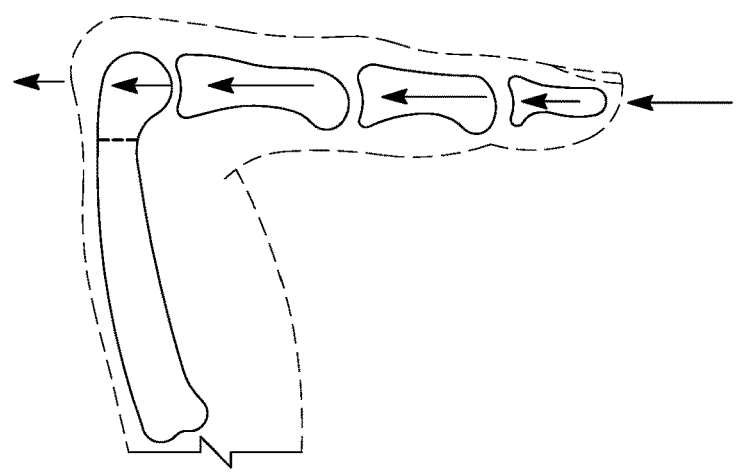

FIGS. 30A-C then show an intraoperative reduction maneuver involving flexion of the MCP (metacarpophalangeal) joint and upward pressure along the length of the finger onto the palmar side of the metacarpal head. These figures thus show the correction of the alignment as one progresses from FIG. 30A to 30C.

Figure 31:
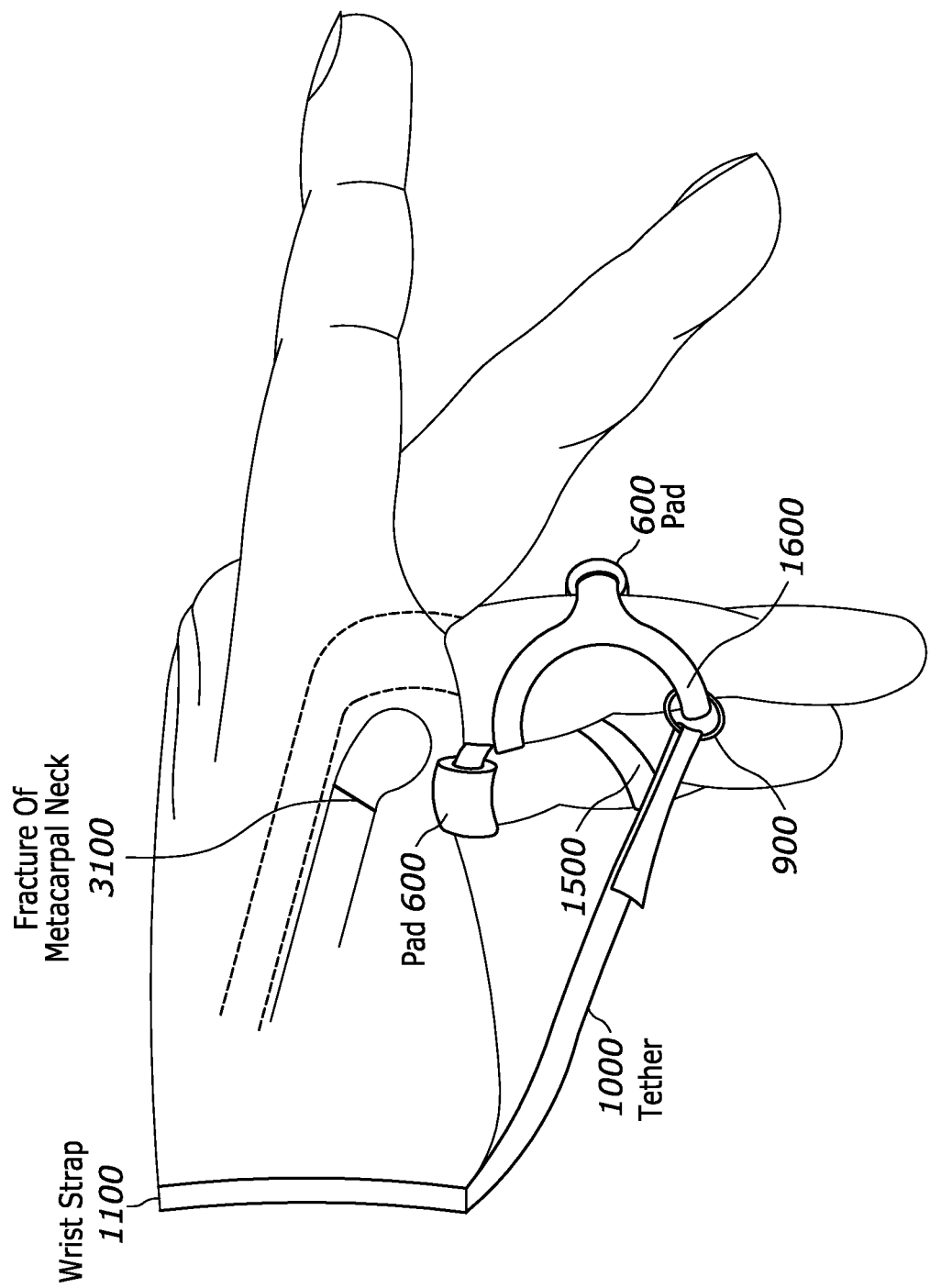
FIG. 31 shows use of staggered/connected finger splints and pads and wrist strap and tether to create a reduction force equal to a surgical reduction maneuver to correct the alignment of a metacarpal neck fracture and stabilize the metacarpal neck fracture consistent with present principles.

Turning to FIG. 31, it shows use of staggered/connected finger splints 1500/1600 and a pad 600 on a dorsal transverse band (like the band 120) of the splint 1600 consistent with present principles. Another pad 600 is also wrapped around a proximal end palmar band (like the band 110) of the splint 1500 (engaged with the non-injured finger used for stabilization). The pads 600 and splints 1500, 1600 thus help stabilize the fracture 3100 of the metacarpal neck due in part to the snug fit this arrangement establishes. A wrist strap 1100 is also shown as attached to a tether 1000 to hold the little and ring fingers flexed through the MCP joint. This reproduces the intraoperative reduction maneuver and maintains this reduced position while the fracture 3100 of the metacarpal neck heals. Thus, a reduction force is created that is equal to a surgical reduction maneuver to correct the alignment of a metacarpal neck fracture and stabilize the metacarpal neck fracture consistent with present principles.

While particular techniques are herein shown and described in detail, it is to be understood that the subject matter which is encompassed by the present invention is limited only by the claims.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

What is claimed is:

1. A device comprising:
   a first splint configured to contact a first finger at three spaced-apart locations of the first finger;
   a second splint configured to contact a second finger at three spaced-apart locations of the second finger, the second splint being laterally connected to the first splint;

a first element mechanically engageable with a portion of the first splint;

a second element mechanically engageable with a non-finger portion of an arm on which the first and second fingers are located; and a connector to connect the first element and the second element to hold the first finger at a desired flexion.

2. The device of claim 1, wherein the connector comprises a strap.

3. The device of claim 2, wherein the strap is adjustable in length to hold the first finger at the desired flexion.

4. The device of claim 1, comprising:

at least a first foam pad removably insertable between the first splint and the first finger.

5. The device of claim 1, comprising first and second foam pads each removably engageable with a different respective portion of the first splint, the different respective portions of the first splint being portions spaced from each other in a proximal-to-distal dimension.

6. The device of claim 1, wherein the portion of the first splint is a palmar portion of the first splint.

7. The device of claim 1, wherein the first element comprises a ring.

8. The device of claim 1, wherein the second element comprises one or more of: a wrist band, a hand band.

9. The device of claim 1, wherein the second splint is offset from the first splint in a proximal-to-distal dimension.

10. The device of claim 1, wherein the second splint is not offset from the first splint in a proximal-to-distal dimension.

11. A device comprising:

a splint configured to contact a finger at three spaced-apart locations of the finger to stabilize the finger;

at least a first foam pad removably insertable between the splint and the finger;

a hollow ring engageable with a palmar portion of the splint;

a wrist band configured to surround a wrist; and a strap to connect the hollow ring and wrist band to hold the finger at a desired flexion.

12. The device of claim 11, wherein the splint is a first splint defining a proximal-to-distal dimension and a lateral dimension, wherein the finger is a first finger, and wherein the device comprises:

at least a second splint configured to contact a second finger at three spaced-apart locations of the second finger, the first and second splints being connected to each other, the second splint being lateral to the first splint and the second splint being offset from the first splint in the proximal-to-distal dimension.

13. The device of claim 11, comprising at least a second foam pad having a thickness different from a thickness of the first foam pad, both foam pads being slitted to accept a segment of the splint to removably individually engage the foam pads with the splint such that a user can select which foam pad to engage with the splint.

14. The device of claim 11, comprising a kit of foam pads of respective different thicknesses.

15. The device of claim 11, wherein the first foam pad is resilient and deformable.

16. The device of claim 11, wherein the three spaced-apart locations are spaced in a proximal-to-distal dimension.

17. The device of claim 11, wherein the splint comprises first, second, and third bands to contact the three spaced-apart locations, the first band configured to contact a dorsal location of the finger and the second and third bands configured to contact palmar locations of the finger.

\* \* \* \* \*